(12) United States Patent
Felix et al.

(10) Patent No.: US 10,166,093 B2
(45) Date of Patent: Jan. 1, 2019

(54) SOFT TISSUE REPAIR PROSTHESIS AND EXPANDABLE DEVICE

(71) Applicant: C.R. Bard, Inc., Murray Hill, NJ (US)

(72) Inventors: Augustus Felix, Cranston, RI (US); Michael F. Jacene, Blackstone, MA (US)

(73) Assignee: C.R. Bard, Inc., Murray Hill, NJ (US)

( * ) Notice: Subject to any disclaimer, the term of this patent is extended or adjusted under 35 U.S.C. 154(b) by 0 days.

(21) Appl. No.: 15/711,886

(22) Filed: Sep. 21, 2017

(65) Prior Publication Data

US 2018/0092725 A1    Apr. 5, 2018

Related U.S. Application Data

(63) Continuation of application No. 13/877,835, filed as application No. PCT/US2011/049732 on Aug. 30, 2011, now Pat. No. 9,808,331.

(Continued)

(51) Int. Cl.
*A61B 17/08* (2006.01)
*A61F 2/00* (2006.01)
(Continued)

(52) U.S. Cl.
CPC ...... *A61F 2/0063* (2013.01); *A61B 17/00234* (2013.01); *A61B 17/3468* (2013.01);
(Continued)

(58) Field of Classification Search
CPC ............. A61B 17/12022; A61F 2/0063; A61F 2002/0072
(Continued)

(56) References Cited

U.S. PATENT DOCUMENTS 460,940 A    10/1891 Baugii
3,857,395 A    12/1974 Johnson et al.
(Continued)

FOREIGN PATENT DOCUMENTS

EP    0 557 963 A1    9/1993
EP    1 336 391 A1    8/2003
(Continued)

OTHER PUBLICATIONS

International Search Report and Written Opinion for Application No. PCT/US11/49732 dated Jan. 6, 2012.
(Continued)

*Primary Examiner* — Melanie Tyson
(74) *Attorney, Agent, or Firm* — Wolf, Greenfield & Sacks, P.C.

(57) ABSTRACT

A hernia repair device is provided which may include a soft tissue repair prosthesis and an expandable device configured to be removably connected with the soft tissue repair prosthesis. Attachment components may be used to removably connect the soft tissue repair prosthesis with the expandable device. The hernia repair device may be manipulated into a reduced configuration for insertion into the body. When expanded, the expandable device may be configured to position the soft tissue repair prosthesis adjacent a hernia defect. The expandable device and/or the attachment components may be shaped and/or configured to minimize the maximum dimension of the hernia repair device in its reduced configuration.

20 Claims, 13 Drawing Sheets

Related U.S. Application Data

(60) Provisional application No. 61/389,792, filed on Oct. 5, 2010.

(51) Int. Cl.
*A61B 17/00* (2006.01)
*A61B 17/34* (2006.01)

(52) U.S. Cl.
CPC ... *A61B 17/0057* (2013.01); *A61F 2002/0072* (2013.01); *A61F 2250/0051* (2013.01)

(58) Field of Classification Search
USPC .................................. 606/151, 192, 195
See application file for complete search history.

(56) References Cited

U.S. PATENT DOCUMENTS

| | | |
|---|---|---|
| 3,863,639 A | 2/1975 | Kleaveland |
| 4,685,447 A | 8/1987 | Iversen et al. |
| 4,769,038 A | 9/1988 | Bendavid et al. |
| 4,823,815 A | 4/1989 | Watson et al. |
| 5,116,357 A | 5/1992 | Eberlach |
| 5,176,692 A | 1/1993 | Wilk |
| 5,263,969 A | 11/1993 | Phillips |
| 5,333,624 A | 8/1994 | Tovey |
| 5,350,388 A | 9/1994 | Epstein |
| 5,366,460 A | 11/1994 | Eberbach |
| 5,370,650 A | 12/1994 | Tovey et al. |
| 5,395,383 A | 3/1995 | Adams et al. |
| 5,397,332 A | 3/1995 | Kammerer et al. |
| 5,405,360 A | 4/1995 | Tovey |
| 5,575,759 A | 11/1996 | Moll et al. |
| 5,607,443 A | 3/1997 | Kierturakis |
| 5,702,416 A | 12/1997 | Kierturakis |
| 5,769,864 A | 6/1998 | Kugel |
| 5,797,960 A | 8/1998 | Stevens et al. |
| 5,824,082 A | 10/1998 | Brown |
| 5,836,871 A | 11/1998 | Wallace et al. |
| 5,836,961 A | 11/1998 | Kierturakis |
| 5,957,939 A | 9/1999 | Heaven et al. |
| 6,168,608 B1 | 1/2001 | Echeverry et al. |
| 6,171,318 B1 | 1/2001 | Kugel et al. |
| 6,174,320 B1 | 1/2001 | Kugel et al. |
| 6,176,863 B1 | 1/2001 | Kugel et al. |
| 6,224,616 B1 | 5/2001 | Kugel |
| 6,258,113 B1 | 7/2001 | Adams et al. |
| 6,302,897 B1 | 10/2001 | Rousseau |
| 6,312,442 B1 | 11/2001 | Kierturakis |
| 6,379,368 B1 | 4/2002 | Corcoran et al. |
| 6,488,653 B1 | 12/2002 | Lombardo |
| 6,551,241 B1 | 4/2003 | Schultz |
| 6,565,590 B2 | 5/2003 | Kierturakis et al. |
| 6,638,292 B2 | 10/2003 | Adams |
| 6,679,900 B2 | 1/2004 | Kierturakis |
| 6,685,714 B2 | 2/2004 | Rousseau |
| 6,702,827 B1 | 3/2004 | Lund et al. |
| 6,755,868 B2 | 6/2004 | Rousseau |
| 6,866,676 B2 | 3/2005 | Kierturakis |
| 6,913,614 B2 | 7/2005 | Marino et al. |
| 7,048,698 B2 | 5/2006 | Whalen et al. |
| 7,101,381 B2 | 9/2006 | Ford et al. |
| 7,128,073 B1 | 10/2006 | van der Burg et al. |
| 7,235,042 B2 | 6/2007 | Vanden Hoek et al. |
| 7,273,489 B2 | 9/2007 | Boudjemline |
| 7,544,213 B2 | 6/2009 | Adams |
| 7,744,617 B2 | 6/2010 | Lunsford et al. |
| 7,780,683 B2 | 8/2010 | Roue et al. |
| 7,947,054 B2 | 5/2011 | Eldar et al. |
| 8,500,762 B2 | 8/2013 | Sholev et al. |
| 8,920,370 B2 | 12/2014 | Sholev et al. |
| 8,920,445 B2 | 12/2014 | Sholev |
| 9,439,643 B2 | 9/2016 | Darois et al. |
| 9,504,548 B2 | 11/2016 | Darois et al. |
| 9,642,689 B2 | 5/2017 | Sholev et al. |
| 9,687,332 B2 | 6/2017 | Sholev et al. |
| 9,808,331 B2 | 11/2017 | Felix et al. |
| 9,861,462 B2 | 1/2018 | Sholev et al. |
| 9,993,324 B2 | 6/2018 | Sholev |
| 2002/0133236 A1 | 9/2002 | Rousseau |
| 2003/0004581 A1 | 1/2003 | Rousseau |
| 2004/0073257 A1 | 4/2004 | Spitz |
| 2004/0087980 A1 | 5/2004 | Ford et al. |
| 2004/0092970 A1 | 5/2004 | Xavier |
| 2004/0097792 A1 | 5/2004 | Moll et al. |
| 2004/0167557 A1 | 8/2004 | Kieturakis et al. |
| 2004/0236363 A1 | 11/2004 | Kieturakis |
| 2005/0033318 A1 | 2/2005 | Miller |
| 2005/0049635 A1 | 3/2005 | Leiboff |
| 2005/0171569 A1 | 8/2005 | Girard et al. |
| 2006/0247586 A1 | 11/2006 | Voegele et al. |
| 2007/0066980 A1 | 3/2007 | Leahy |
| 2007/0078477 A1 | 4/2007 | Heneveld et al. |
| 2007/0100369 A1 | 5/2007 | Cragg et al. |
| 2007/0185506 A1 | 8/2007 | Jackson |
| 2007/0260179 A1 | 11/2007 | Sholev et al. |
| 2008/0033461 A1 | 2/2008 | Koeckerling et al. |
| 2008/0065229 A1 | 3/2008 | Adams |
| 2008/0195121 A1 | 8/2008 | Eldar et al. |
| 2009/0012350 A1 | 1/2009 | Tihon |
| 2009/0082792 A1 | 3/2009 | Koyfman et al. |
| 2009/0254103 A1 | 10/2009 | Deutsch |
| 2010/0069947 A1 | 3/2010 | Sholev et al. |
| 2010/0137999 A1 | 6/2010 | Shohat |
| 2010/0292718 A1* | 11/2010 | Sholev ............. A61B 17/00234 606/151 |
| 2011/0112560 A1 | 5/2011 | Sholev |
| 2011/0295283 A1 | 12/2011 | Darois et al. |
| 2013/0218179 A1 | 8/2013 | Sholev et al. |
| 2013/0231526 A1 | 9/2013 | Felix et al. |
| 2014/0051915 A1 | 2/2014 | Sholev et al. |
| 2015/0196377 A1 | 7/2015 | Sholev et al. |
| 2015/0202035 A1 | 7/2015 | Sholev |
| 2017/0100229 A1 | 4/2017 | Darois et al. |
| 2017/0290577 A1 | 10/2017 | Sholev et al. |

FOREIGN PATENT DOCUMENTS

| | | |
|---|---|---|
| EP | 1 454 599 A2 | 9/2004 |
| GB | 2 397 239 A | 7/2004 |
| JP | 2000-501634 A | 2/2000 |
| JP | 2007-275203 A | 10/2007 |
| JP | 2008-520372 A | 6/2008 |
| WO | WO 95/30374 A1 | 11/1995 |
| WO | WO 96/00531 A1 | 1/1996 |
| WO | WO 97/21461 A1 | 6/1997 |
| WO | WO 2005/046511 A2 | 5/2005 |
| WO | WO 2006/040760 A2 | 4/2006 |
| WO | WO 2006/055823 A2 | 5/2006 |
| WO | WO 2007/030676 A2 | 3/2007 |
| WO | WO 2007/115110 A2 | 10/2007 |
| WO | WO 2008/045635 A2 | 4/2008 |
| WO | WO 2008/065653 A1 | 6/2008 |
| WO | WO 2009/050717 A2 | 4/2009 |

OTHER PUBLICATIONS

International Preliminary Report on Patentability for Application No. PCT/US11/49732 dated Apr. 18, 2013.

Extended European Search Report dated Sep. 5, 2017 in connection with European Application No. 17167634.9.

* cited by examiner

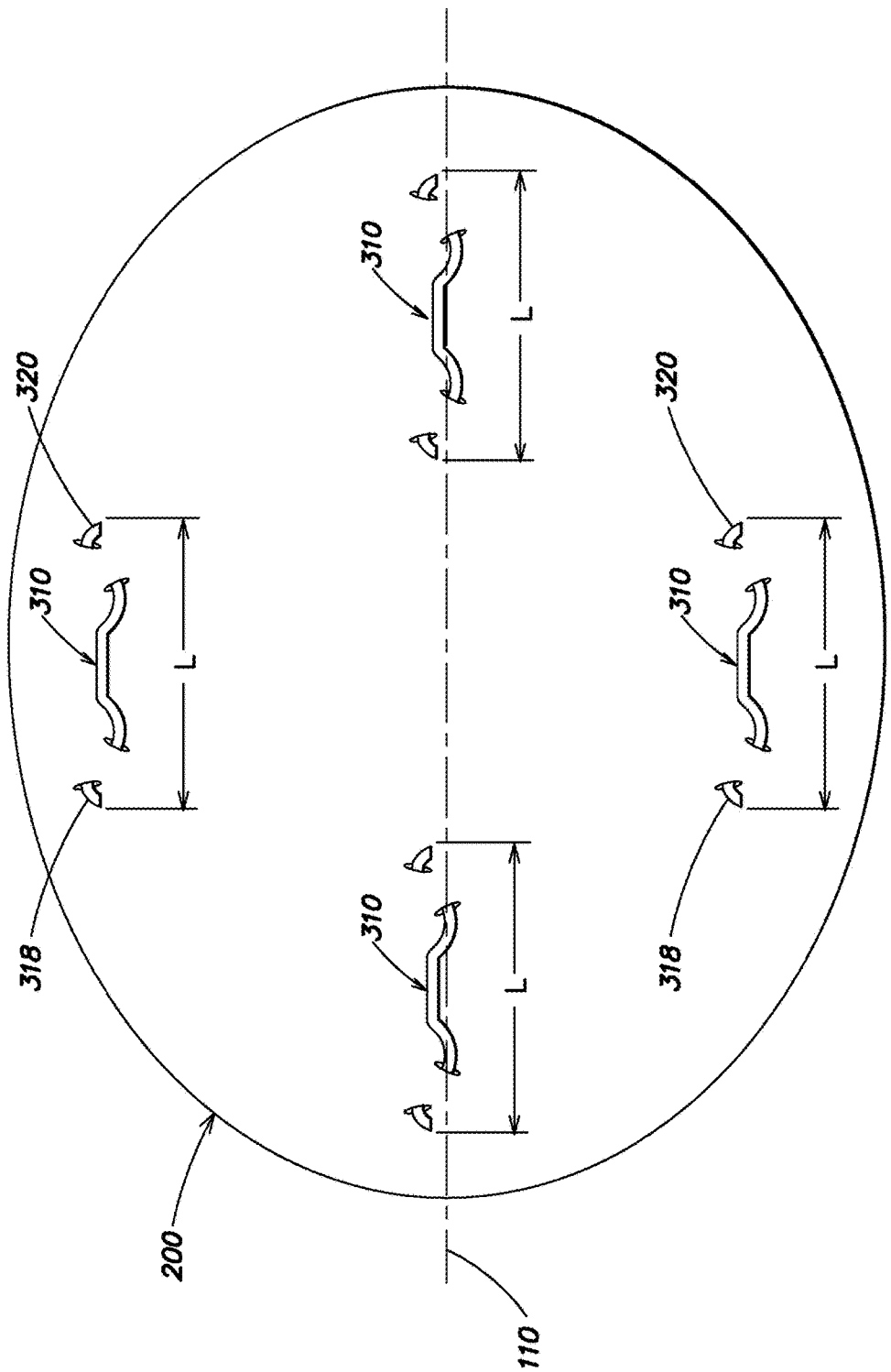

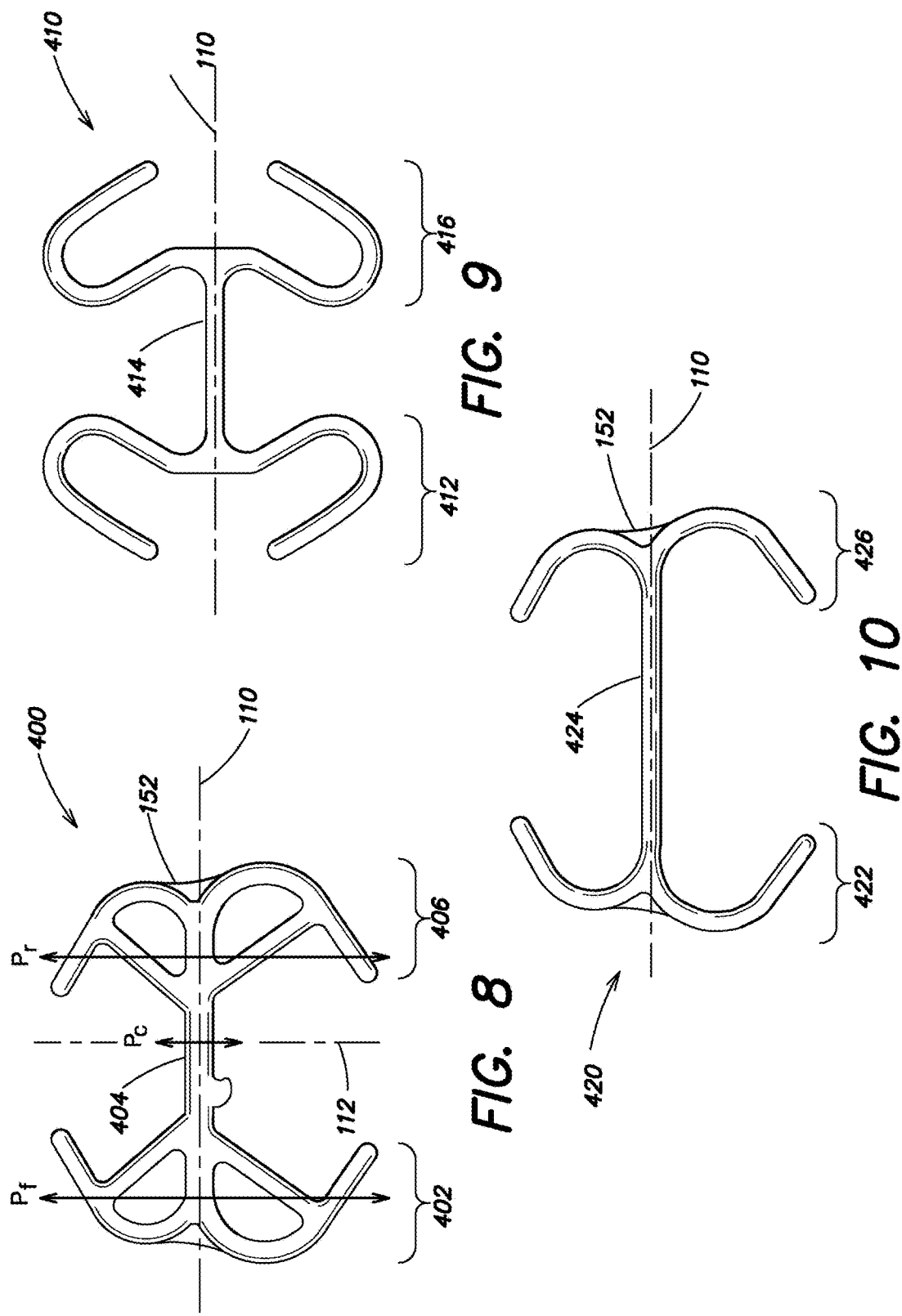

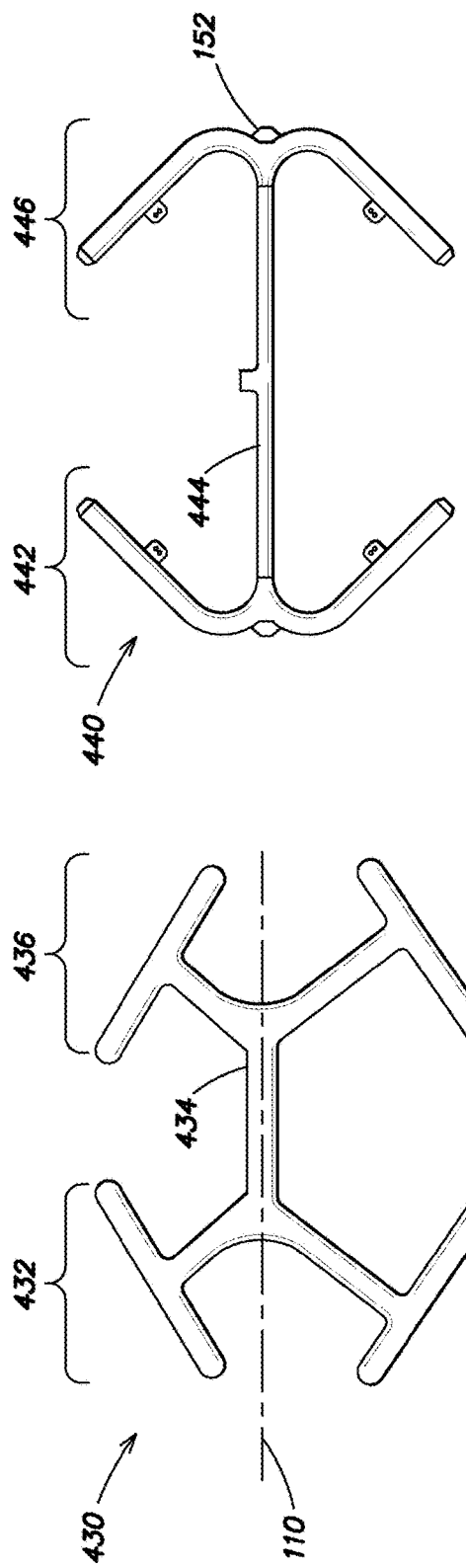
FIG. 11
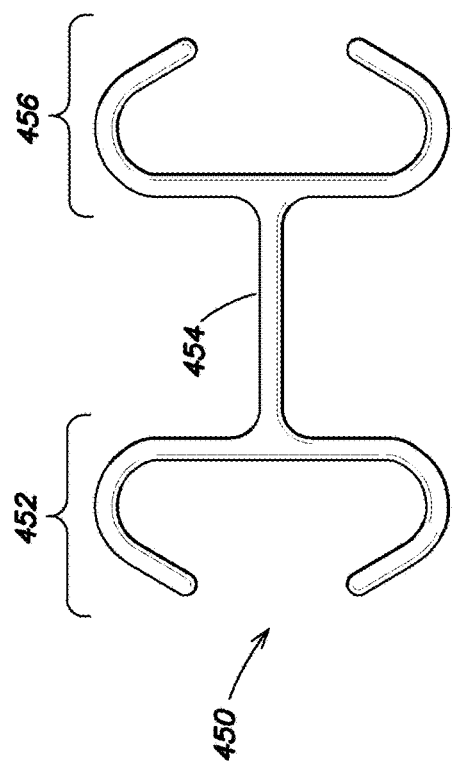
FIG. 12
FIG. 13

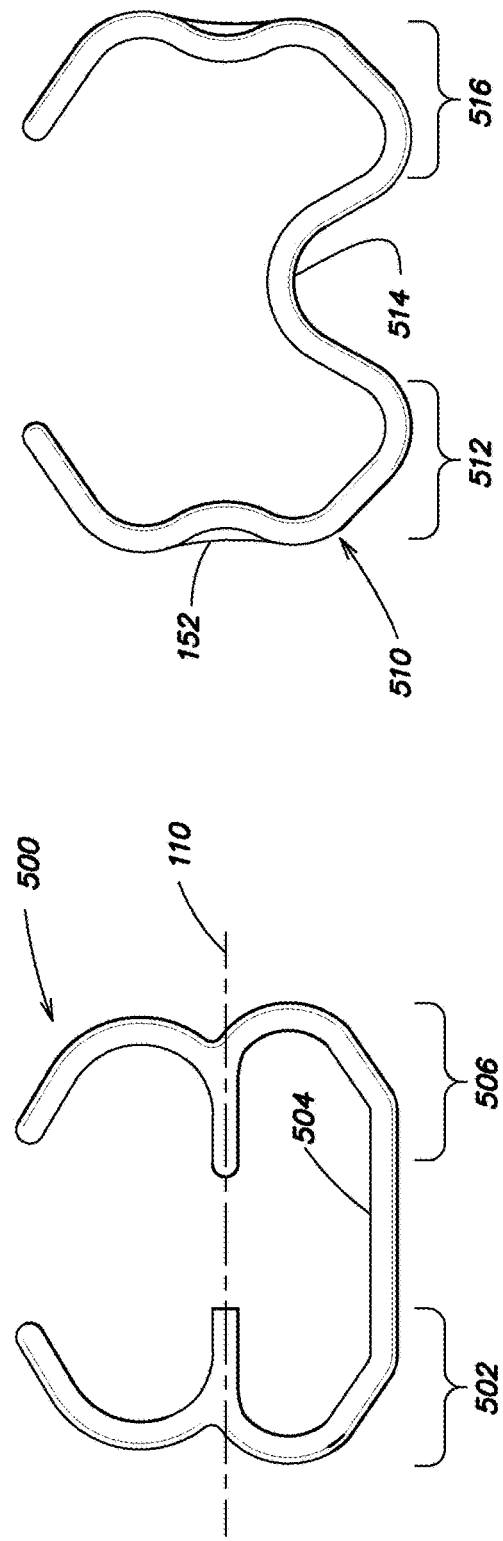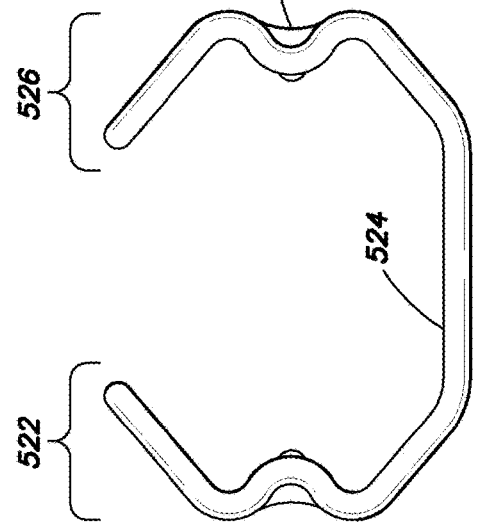

SOFT TISSUE REPAIR PROSTHESIS AND EXPANDABLE DEVICE

RELATED APPLICATIONS

This application is a continuation of U.S. patent application Ser. No. 13/877,835, now U.S. Pat. No. 9,808,331, which is a national stage filing under 35 U.S.C. § 371 of International Application No. PCT/US2011/049732, filed on Aug. 30, 2011, entitled "SOFT TISSUE REPAIR PROSTHESIS AND EXPANDABLE DEVICE," which claims the benefit of U.S. provisional application No. 61/389,792, filed on Oct. 5, 2010, entitled "SOFT TISSUE REPAIR PROSTHESIS AND EXPANDABLE DEVICE," each of which are incorporated by reference herein in their entireties.

FIELD OF INVENTION

The present invention is directed to a soft tissue repair prosthesis, an expandable device, and to attachment components for removably securing the prosthesis with the expandable device.

BACKGROUND OF INVENTION

One technique for repairing a soft tissue defect, such as an abdominal wall hernia, involves inserting a soft tissue repair prosthesis, such as a mesh patch or plug, into an intra-abdominal space, positioning the prosthesis relative to the wall defect, and then, if desired, securing the prosthesis with tacks, sutures, and/or adhesives.

To deliver the prosthesis intra-abdominally, the prosthesis may be rolled up, folded or otherwise collapsed into a reduced configuration and then inserted through a small incision or a trocar and into the intra-abdominal space. The prosthesis is then unfurled and positioned relative to the defect.

SUMMARY OF INVENTION

In one illustrative embodiment, a hernia repair device is provided which includes an expandable device configured to be removably connected with a soft tissue repair prosthesis, the expandable device having a first axis and a second axis, the first axis being substantially perpendicular to the second axis, and where the second axis defines a maximum width of the expandable device. The expandable device is configured to be manipulated about the first axis into a reduced configuration for insertion into a body. The hernia repair device further includes a plurality of attachment components associated with the expandable device to removably connect the prosthesis with the expandable device and the plurality of attachment components are offset from the second axis.

In another illustrative embodiment, a hernia repair device is provided which includes an expandable device configured to be removably connected with a soft tissue repair prosthesis, the expandable device having a first axis and a second axis, the first axis being substantially perpendicular to the second axis, and the first axis intersecting the second axis at approximately the center of the expandable device. The expandable device is configured to be manipulated about the first axis into a reduced configuration for insertion into a body. The expandable device includes an expandable forward portion spaced apart from an expandable rear portion by a single intermediate portion which connects the forward portion to the rear portion. The forward portion and the rear portion each include sections that extend outwardly from the first axis. A maximum dimension of the intermediate portion in the reduced configuration along a plane defined by the second axis is less than a maximum dimension of the expandable device at either the forward portion and the rear portion in the reduced configuration defined along a plane substantially parallel to the second axis.

In yet another illustrative embodiment, a hernia repair device is provided which includes an expandable device configured to be removably connected with a soft tissue repair prosthesis, the expandable device having a first axis, where the expandable device is configured to be manipulated about the first axis into a reduced configuration for insertion into a body. The hernia repair device further includes a plurality of attachment components coupled to the expandable device to removably connect the prosthesis with the expandable device. At least one of the plurality of attachment components has a maximum dimension which defines a longitudinal axis of the attachment component, and to minimize the size of the hernia repair device in its reduced configuration, the at least one of the plurality of attachment components is arranged on the expandable device such that its longitudinal axis is substantially parallel to the first axis.

In yet a further illustrative embodiment, a hernia repair device is provided which includes an expandable device configured to be removably connected with a soft tissue repair prosthesis and a plurality of attachment components coupled to the expandable device to removably connect the prosthesis with the expandable device. The plurality of attachment components are positioned to extend entirely within the perimeter of the expandable device.

In another illustrative embodiment, a hernia repair device is provided which includes a soft tissue repair prosthesis, and an expandable device removably connected with the soft tissue repair prosthesis, the expandable device having a first axis and a second axis, the first axis being substantially perpendicular to the second axis, and where the second axis defines a maximum width of the expandable device. The expandable device is configured to be manipulated about the first axis into a reduced configuration for insertion into a body. The soft tissue repair prosthesis has a maximum width defined in a direction substantially parallel to the second axis, and to minimize the size of the hernia repair device in its reduced configuration, the maximum width of the expandable device is spaced apart from the maximum width of the soft tissue repair prosthesis.

In yet a further illustrative embodiment, a hernia repair device is provided which includes an inflatable device configured to be removably connected with a soft tissue repair prosthesis, the inflatable device having a first axis where, when deflated, the inflatable device is configured to be manipulated about the first axis into a reduced configuration for insertion into a body. The inflatable device includes a plurality of reliefs spaced around the perimeter of the inflatable device configured to minimize bending of the inflatable device when inflated.

In another illustrative embodiment, a method of assembling a hernia repair device is provided. The method includes the acts of arranging a soft tissue repair prosthesis on an expandable device with at least one attachment component, where the prosthesis, expandable device and attachment component form a hernia repair device. The method further includes manipulating the hernia repair device about a first axis into a reduced configuration, where the soft tissue repair prosthesis is arranged on the expansion device such that a maximum dimension of the hernia repair device in the reduced configuration is minimized.

Various embodiments of the present invention provide certain advantages. Not all embodiments of the invention share the same advantages and those that do may not share them under all circumstances.

Further features and advantages of the present invention, as well as the structure of various embodiments that incorporate aspects of the invention are described in detail below with reference to the accompanying drawings.

BRIEF DESCRIPTION OF DRAWINGS

The foregoing and other objects and advantages of the invention will be appreciated more fully from the following drawings, wherein like reference characters designate like features, in which:

FIG. 2A illustrates the attachment component shown in FIG. 2 coupled to a soft tissue repair prosthesis;

FIGS. 8-28 illustrate expandable devices according to various embodiments of the present invention.

DETAILED DESCRIPTION

Figure 1A:
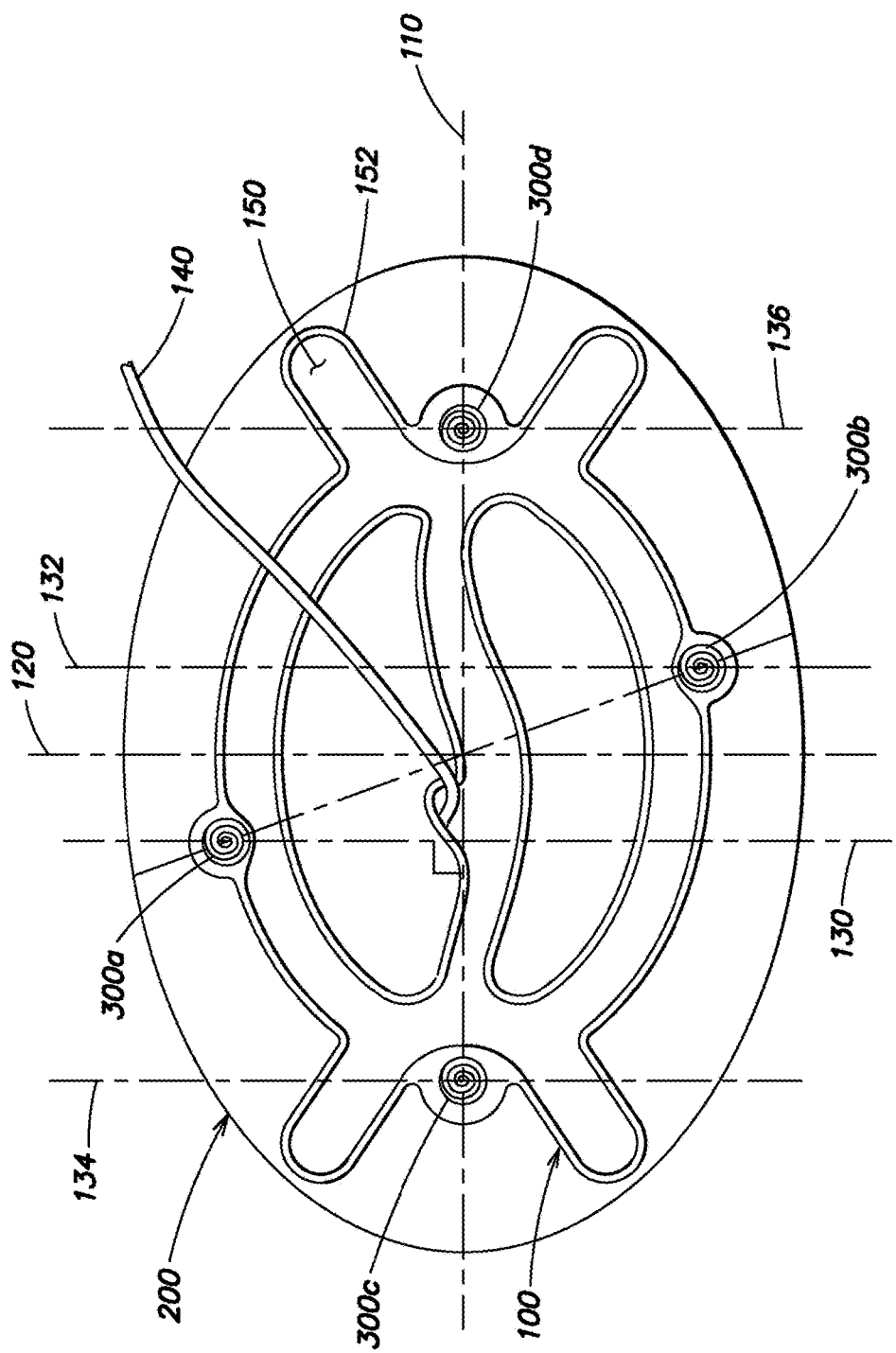
FIG. 1A is a top view of an expandable device and soft tissue repair prosthesis according to one embodiment of the present invention.
Figure 1B:
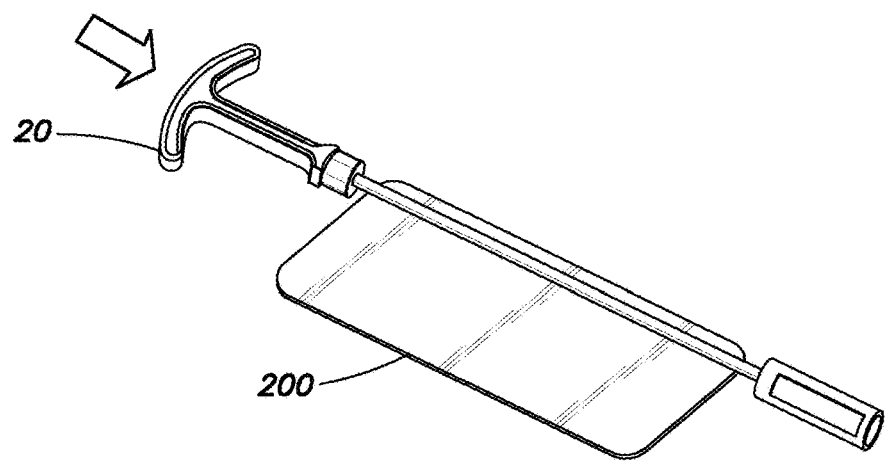
FIGS. 1B, 1C and 1D are perspective views illustrating a hernia repair device being manipulated into a reduced configuration.

Aspects of the present invention are directed to a soft tissue repair prosthesis, such as a patch, plug, or patch and plug combination, for augmenting, reconstructing or otherwise repairing a muscle or tissue wall, such as a chest wall or abdominal wall, and that has particular application for repairing a hernia defect to reconstruct the chest wall.

An expandable device may be provided for delivering, locating, or otherwise positioning the soft tissue repair prosthesis at the surgical site. The soft tissue repair prosthesis may be carried by or otherwise connected with the expandable device, such that manipulation of the expandable device will effect the shape and/or position of the soft tissue repair prosthesis. The expandable device may have a reduced configuration suitable for introduction to the surgical site and an expanded configuration for deploying, locating, or otherwise positioning the soft tissue repair prosthesis. Expansion of the expandable device, when connected with the soft tissue repair prosthesis, may cause the soft tissue repair prosthesis to transform from a reduced delivery profile to an enlarged configuration suitable for the desired procedure, such as extending over, under, or filling a hernia defect. The term "hernia repair device" is used throughout the application and may be used to reference the expandable device, the soft tissue repair prosthesis, and/or the combination of the expandable device and soft tissue repair prosthesis, as the invention is not limited in this respect.

As set forth below, the expandable device may be in the form of a balloon or other inflatable bladder, or other construction suitable for delivery in a reduced configuration and expansion to a larger size. The soft tissue repair prosthesis may be mounted to, or otherwise connected with, the expandable device, and then the combined components may be reduced in size, such as by rolling, folding, collapsing, or otherwise manipulating, and then inserted through a trocar or small incision into the abdominal cavity or other surgical site. Expansion of the expandable device, such as by inflation where the expandable device is in the form of a balloon, will in turn cause the soft tissue repair prosthesis to move into an expanded configuration suitable for the intended procedure. For example, where the soft tissue repair prosthesis is a mesh sheet and has been rolled up with an associated balloon, inflation of the balloon will cause the mesh sheet to unroll or otherwise expand into an enlarged configuration which can then be positioned relative to the defect.

Aspects of the present invention are directed to arrangements for connecting an expandable device with a soft tissue repair prosthesis. In one embodiment, the expandable device and soft tissue repair prosthesis are detachably connected. For example, and without limitation, one or more attachment components may releasably connect the expandable device and soft tissue repair prosthesis. The attachment components may loosely connect the prosthesis and the expandable device together in the reduced profile. As set forth in greater detail below, the attachment components may be configured and arranged to minimize the size of the hernia repair device in its reduced configuration.

Other aspects of the present invention are directed to various configurations for the expandable device to minimize the size of the hernia repair device when in its reduced configuration.

Turning to FIG. 1A, one embodiment of a hernia repair device is illustrated. The hernia repair device includes an expandable device 100 that is configured to be removably connected with a soft tissue repair prosthesis 200. A plurality of attachment components 300a, 300b, 300c, 300d are provided to removably connect the prosthesis 200 with the expandable device 100. In this particular embodiment, the attachment components 300a-d are configured as substantially helical shaped coils that may be oriented to extend into/out of the page. As discussed below, in other embodiments, other types of attachment components are also contemplated as the invention is not so limited.

Applicant recognized the importance of minimizing the size of the hernia repair device when in its reduced configuration for insertion into a body. The hernia repair device is typically inserted through a small incision or a trocar and into the intra-abdominal space. It may be desirable to minimize the size of the incision or trocar. For example, in one particular embodiment, it may be desirable to use a trocar that is 12 mm or less, which would require that the outer diameter, or other maximum dimension, of the hernia repair device in its reduced configuration is 12 mm or less. In another embodiment, it may be desirable to use a trocar that is 20 mm or less, which would require that the outer diameter, or other maximum dimension, of the hernia repair device in its reduced configuration is 20 mm or less. It should be appreciated that when the hernia repair device is rolled into a cylindrical configuration, it may have a diameter, but that in embodiments where the hernia repair device is folded or otherwise manipulated into its reduced configuration, the device may have a non-circular cross-section and will still have a maximum dimension. The term "maximum dimension" is used throughout the application and may be used to reference this outer dimension of the hernia repair device, or components of the hernia repair device, when in the reduced configuration.

As set forth below, Applicant recognized that the particular placement of the attachment components relative to the expandable device and/or prosthesis may be optimized to minimize the maximum dimension of the hernia repair device in its reduced configuration. Applicant recognized that the attachment components may be thicker than the prosthesis and/or the expandable device, and thus, strategic placement of the attachment components may help to minimize the maximum dimension of the hernia repair device when in its reduced configuration. This may help to minimize the size of the incision or trocar needed to delivery the hernia repair device into the body. For example, as discussed in greater detail below, in one embodiment, the attachment components may be offset from the maximum width portion of the expandable device and/or prosthesis. As set forth below, in another embodiment, the attachment components may be positioned relative to the expandable device such that two attachment components are not stacked onto each other when the hernia repair device is manipulated into its reduced configuration.

As illustrated in FIG. 1A, the expandable device 100 has a first axis 110 and the expandable device 100 is configured to be furled, or otherwise manipulated, about the first axis 110 into a reduced configuration for insertion into a body. Thus, the first axis 110 may also be referred to as the furling axis, rolling axis, or manipulation axis. The expandable device also has a second axis 120 which is substantially perpendicular to the first axis. As shown, the second axis 120 defines a maximum width of the expandable device 100 in a plane substantially perpendicular to the first axis 110. In this particular illustrative embodiment, the first axis 110 intersects the second axis 120 at approximately the center of the expandable device. However, it should be appreciated that in another embodiment where the expandable device is shaped differently, the first axis 110 may intersect the second axis 120 at a location spaced apart from the center of the expandable device.

As illustrated in FIG. 1A, a plurality of attachment components 300a, 300b, 300c, 300d are associated with the expandable device 100 to removably connect the prosthesis 200 with the expandable device 100. In this particular embodiment, the attachment components 300a-d are mechanical fasteners coupled to the expandable device 100. More specifically, as illustrated, the attachment components 300a-d are configured as substantially helical shaped coils, where a portion of the coil, such as one end of the coil, is secured to the expandable device, and may, for example pierce through a portion of the expandable device 100. As set forth in more detail below, in other embodiments, the attachment components may be configured differently as the invention is not limited in this respect.

Regardless of the specific type of attachment component, in this embodiment, the attachment components 300a-d are offset from the second axis 120. As mentioned above, the second axis 120 defines a maximum width of the expandable device 100. Thus, by offsetting the attachment components from the second axis 120, the attachment components are offset from the maximum width of the expandable device 100.

As shown in FIG. 1A, in one embodiment, the prosthesis is substantially elliptical shaped, such that the maximum width of the prosthesis 200 is also along the second axis 120. Thus, in this particular embodiment, the attachment components 300a-d are also offset from the portion of the prosthesis 200 having a maximum width. Applicant recognized that offsetting the attachment components 300a-d from the maximum width of the expandable device 100 and/or the maximum width of the prosthesis 200 may minimize the maximum dimension of the hernia repair device when the device is rolled or otherwise manipulated into in its reduced configuration.

In one embodiment, the maximum dimension of the expandable device 100 in its reduced configuration is greater along the second axis 120 (i.e. at its location of maximum width). In the particular embodiment illustrated in FIG. 1, the maximum dimension of the prosthesis 200 in its reduced configuration will also be greatest along the second axis. It is recognized that the attachment components 300a-d may also contribute to the maximum dimension of the hernia repair device. As illustrated, in one embodiment, the attachment components 300a-d are spaced apart, such that the thickness of the attachment components 300a-d may vary across the length of the prosthesis and the expandable device. By spacing the attachment components away from the maximum width of the expandable device and/or prosthesis when in an expanded flat configuration, the attachment components may minimally contribute to the maximum dimension of the hernia repair device, such that the maximum dimension of the hernia repair device in its reduced configuration is minimized.

In one embodiment, an attachment component 300a is positioned near the second axis 120 along a plane 130 defined as being substantially perpendicular to the first axis 110 (i.e. manipulation axis). Applicant recognized that if multiple attachment components are positioned along plane 130, then the attachment components will stack on top of each other when the hernia repair device is manipulated into its reduced configuration. Thus, the multiple attachment components along that plane will cause the maximum dimension of the device in its reduced configuration to be greater than if only one attachment component is positioned along the plane 130. In one embodiment, to minimize the maximum dimension of the hernia repair device in its reduced configuration, no other attachment component is arranged on that same plane 130. In this respect, as the expandable device 100 is folded, rolled, or otherwise manipulated into its reduced configuration, one attachment component 300a is not stacked onto another attachment component 300b. By offsetting the attachment components 300a-d across the length of the hernia repair device, the maximum dimension of the hernia repair device may be minimized when in its reduced configuration.

In this embodiment, each attachment component 300a-d is positioned along a plane that is defined as being substantially perpendicular to the first axis (i.e. manipulation axis) and no other attachment component is also arranged on that same plane. For example, as illustrated, attachment component 300a is positioned on plane 130, attachment component 300b is positioned on plane 132, attachment component 300c is positioned on plane 134, and attachment component 300d is positioned on plane 136. As illustrated, because all of these planes are substantially perpendicular to the first axis 110 (i.e. manipulation axis), these planes are also substantially parallel to each other.

In the particular embodiment illustrated in FIG. 1A, the length of the expandable device 100 along the first axis 110 is greater than the width of the expandable device 100 along the second axis 120. In certain embodiments, this may be preferred so that when the expandable device 100 is manipulated into its reduced configuration for insertion into the body, the device is furled, or otherwise manipulated, about its larger dimension so that it has a more slender reduced configuration. It should be appreciated that in other embodiments, the length of the expandable device 100 along the first axis 110 may be substantially equal to the width of the expandable device 100 along the second axis 120, and in yet other embodiments, the length of the device 100 may be less than the width, as the invention is not so limited.

Figure 1C:
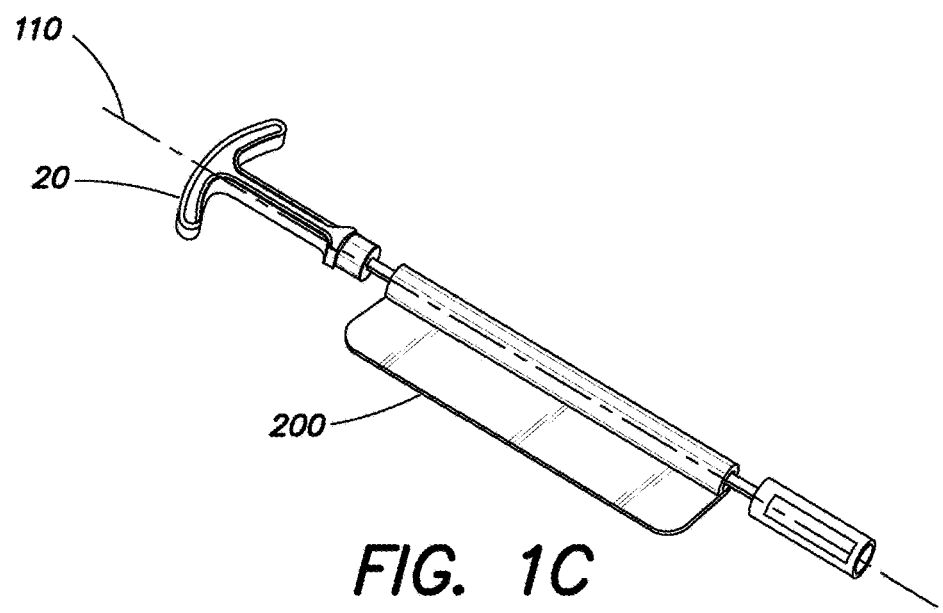
Figure 1D:
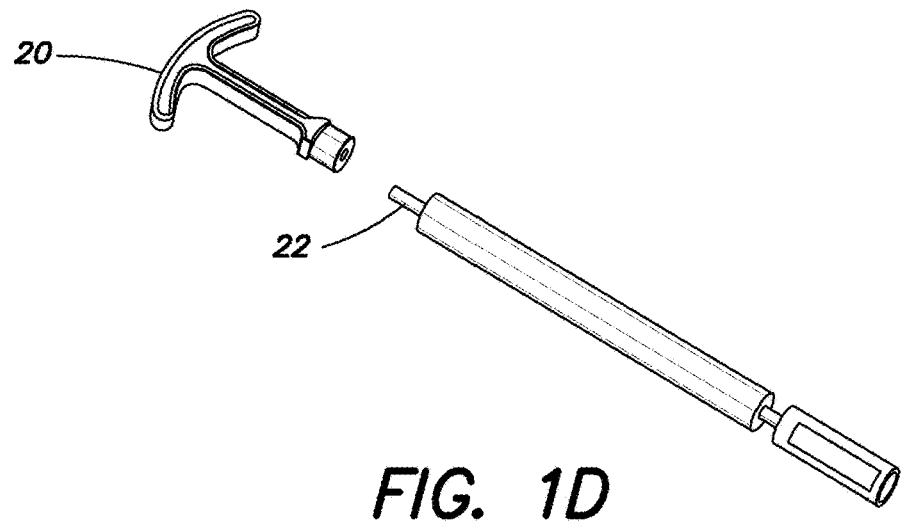

The hernia repair device illustrated in FIG. 1A is shown with the expandable device 100 and the prosthesis 200 both having a substantially planar configuration. As discussed above, and as illustrated in FIGS. 1B-1D, the hernia repair device may be manipulated into a reduced configuration for insertion into the body. As illustrated, a device 20 may be used to manipulate the hernia repair device into its reduced configuration. For simplification of the drawings, in FIGS. 1B-1C, only the prosthesis 200 is illustrated and the expandable device 100 is not shown. As mentioned above, the hernia repair device may be furled, rolled, or otherwise manipulated about the first axis 110 into its reduced configuration. As shown in FIG. 1C, in which the prosthesis 200 is partially rolled up, the first axis 110 (which may be considered the manipulation axis) aligns with the longitudinal axis of the device 20 used to manipulate the hernia repair device into its reduced configuration. It should also be appreciated that the hernia repair device may be folded, crumpled, collapsed or otherwise manipulated about the first axis 110 into its reduced configuration.

In one embodiment, the expandable device 100 is inflatable (either filled with a gas or a liquid). As shown in FIG. 1A, an inflation tube 140 may be coupled to the expandable device 100 for selectively inflating the device. In this particular embodiment, the inflation tube is coupled to the center portion of the expandable device, but it should be appreciated that the inflation tube may be coupled to the expandable device in a different location. It should be recognized that before the hernia repair device is inserted into the body that the expandable device 100 may be in a deflated state. The expandable device 100 may not be inflated until after it is within the body. In one particular embodiment, the expandable device 100 is inflatable with air.

The expandable device 100 may be removably connected with the soft tissue repair prosthesis 200 by one or more attachment components 300, including, but not limited to sutures, adhesives, or mechanical fasteners including hook and loop fasteners, rivets, coils, and the like. As discussed above, in one embodiment, the attachment components 300a-d are configured as substantially helical shaped coils that extend into/out of the page, where a portion of the coil is secured to the expandable device, and may, for example pierce through a portion of the expandable device 100.

Applicant recognized that the shape and orientation of the attachment components relative to the expandable device and/or the prosthesis may affect the maximum dimension of the hernia repair device when in its reduced configuration. In particular, applicant determined that by orienting the attachment component such that the maximum dimension of the attachment component is aligned with the first axis 110 (i.e. manipulation axis), the maximum dimension of the hernia repair device in its reduced configuration may be minimized. As mentioned above, it may be desirable to minimize the maximum dimension of the hernia repair device in its reduced configuration so that a smaller incision or trocar can be used to delivery the hernia repair device into the body. This concept will be discussed in greater detail with respect to FIGS. 2-7, which disclose some of the various embodiments of attachment components in accordance with aspects of the present invention.

Figure 2:
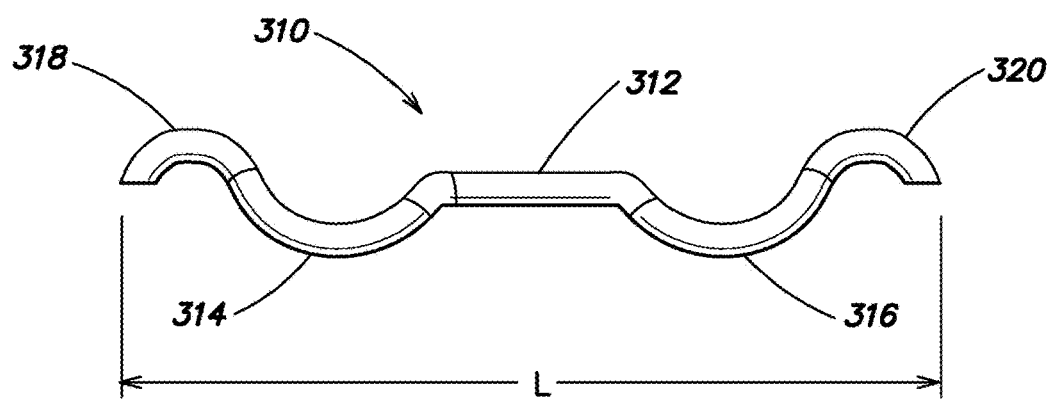
FIG. 2 illustrates an attachment component according to one embodiment of the present invention.

The attachment component 310 shown in FIG. 2 has a substantially linear center portion 312 with two curved portions 314, 316 positioned on each side of the linear portion 312. Two additional curved portions 318, 320 are positioned on each side of the curved portions 314, 316, and they are curved in the opposite direction as the curved portions 314, 316, such that the two adjacent portions form a substantially S-shaped curve. A portion of the attachment component, such as the center portion 312 may be coupled to the expandable device 100. For example, in one embodiment, the center portion 312 may be welded, or otherwise secured to the expandable device 100. As shown in FIG. 2A, one or both of the S-shaped ends of the attachment component 310 may be used to hook or otherwise couple the prosthesis 200 to the attachment component 310 and the expandable device 100. These curved ends of the attachment component 310 may assist to retain the prosthesis 200 to the expandable device 100.

The attachment component 310 has a length L which defines its maximum dimension and defines its longitudinal axis. As shown in FIG. 2A, to minimize the maximum dimension of the hernia repair device in its reduced configuration, the attachment component 310 may be arranged on the hernia repair device such that its longitudinal axis is substantially parallel to the first axis 110. For simplification, in FIG. 2A, the prosthesis 200 is illustrated, but the expandable device 100 is not shown. In this respect, as the hernia repair device is furled, rolled, or otherwise manipulated about the first axis 110 into its reduced configuration, the attachment component 310 is oriented to minimally contribute to the maximum dimension of the hernia repair device when the device is manipulated into its reduced configuration. It should be appreciated that if the attachment component 310 is made of a substantially rigid material and is oriented such that its longitudinal axis was, for example, substantially perpendicular to the first axis 110 (i.e. substantially parallel to the second axis 120), then the maximum dimension of the hernia repair device in its reduced configuration may be at least as big as the length L of the attachment component 310, which may be undesirably too large.

Figure 3:
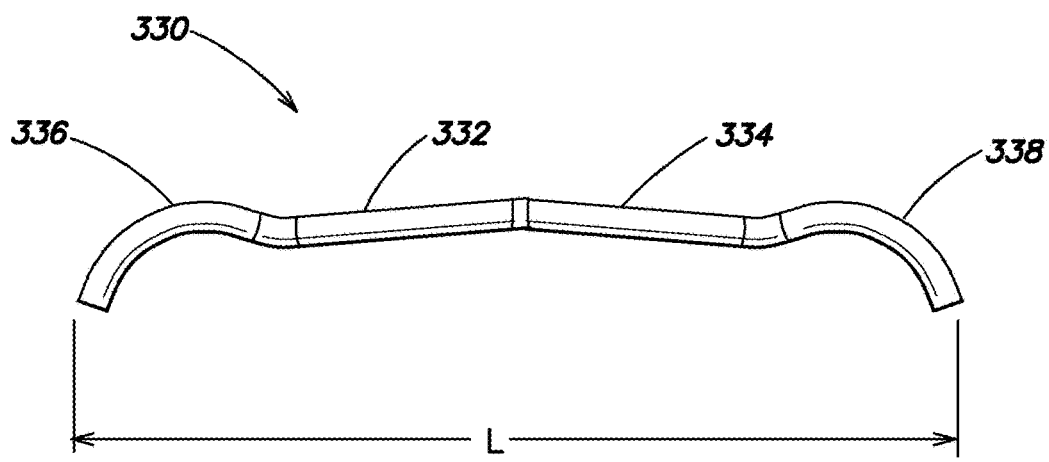
FIG. 3-7 illustrate attachment components according to various embodiments of the present invention.

FIG. 3 illustrates another embodiment of an attachment component 330 which includes two substantially linear center portion 332, 334 with two curved portions 336, 338 positioned on each side of the linear portions 332, 334. As shown, the two center portions 332, 334 may form a substantially V-shape at the center of the attachment component 330. A portion of the attachment component 330, such as one or both of the center portions 332, 334 may be coupled to the expandable device 100. One or both of the curved end portions 336, 338 of the attachment component 330 may be used to hook or otherwise couple the prosthesis 200 to the attachment component 330 and the expandable device 100. The attachment component 330 has a length L which defines its maximum dimension and defines its longitudinal axis. As discussed above with respect to attachment component 310, the attachment component 330 may be arranged on the expandable device such that its longitudinal axis is substantially parallel to the first axis 110 (see FIG. 2A.) In this respect, as the hernia repair device is furled, rolled, or otherwise manipulated about the first axis 110 into its reduced configuration, the attachment component 330 is oriented to minimally contribute to the maximum dimension of the hernia repair device in its reduced configuration.

Figure 4:
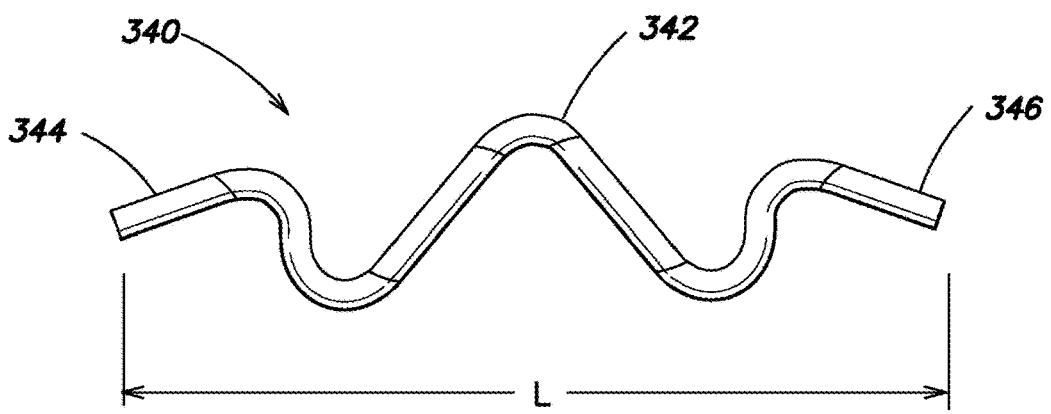
Figure 5:
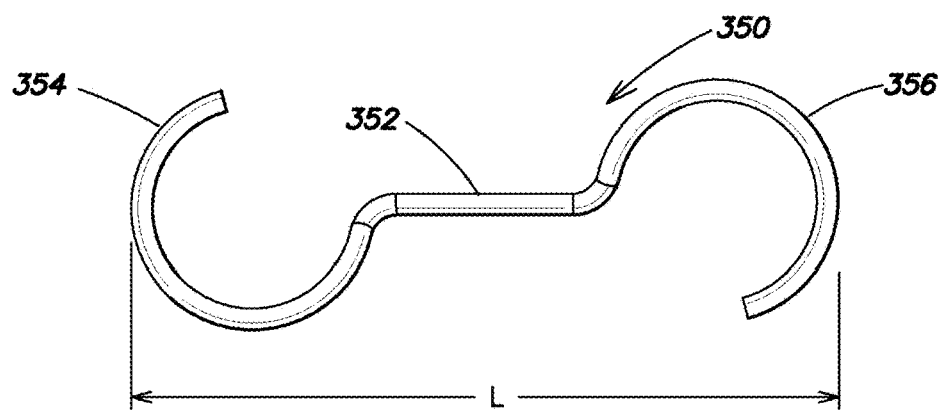
Figure 6:
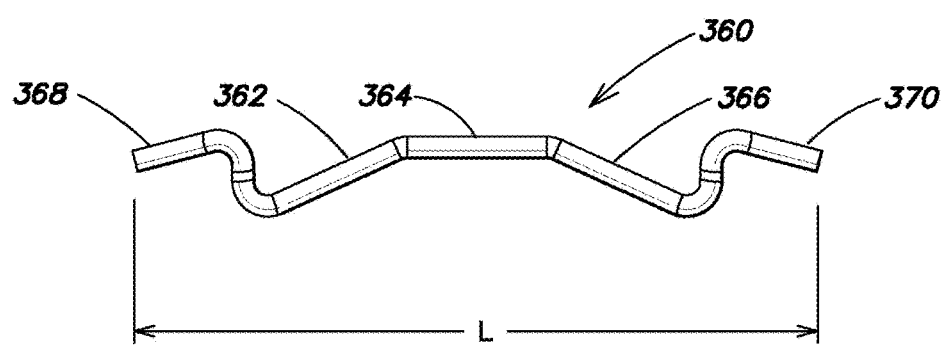
Figure 7:
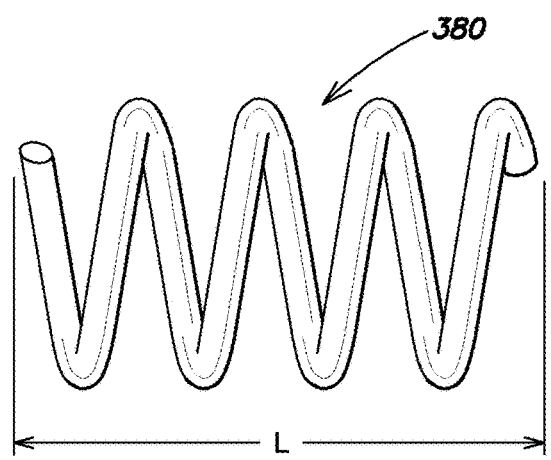

FIGS. 4-7 illustrate additional attachment components in accordance with aspects of the present invention. In particular, FIG. 4 illustrates an attachment component 340 that has a V-shaped center portion 342, with a substantially S-shaped portion 344, 346 on each end of the attachment component 340. FIG. 5 illustrates an attachment component 350 that has a substantially linear center portion 352, with a substantially C-shaped portion 354, 356 on each end of the attachment component 350. FIG. 6 illustrates an attachment component 360 with a plurality of substantially linear center portions 362, 364, 366 with a substantially S-shaped portion 368, 370 on each end of the attachment component 360. Finally, FIG. 7 illustrates yet another embodiment of an attachment component 380. In this particular embodiment, the attachment component 380 is substantially helical shaped. As illustrated, each of these attachment component 340, 350, 360, 380 has a length L which defines its maximum dimension and defines its longitudinal axis. As discussed above with respect to attachment components 310, 330, the attachment components 340, 350, 360, 380 may be arranged on the expandable device such that its longitudinal axis is substantially parallel to the first axis 110 (see FIG. 2A.) In this respect, as the hernia repair device is furled, rolled, or otherwise manipulated about the first axis 110 into its reduced configuration, the attachment component 340, 350, 360, 380 is oriented to minimally contribute to the maximum dimension of the hernia repair device in its reduced configuration.

The attachment components may be formed from a variety of types of materials, as the invention is not so limited. In one embodiment, the attachment components are made from a plastic or a metal material such as, but not limited to a shape memory metal, polyurethane, or nylon heat sealed into its specific configuration. In one embodiment the attachment components are made of a substantially rigid material such that the attachment component substantially maintains its shape and configuration.

In one embodiment, the attachment component is made of an elastic or spring-like material which enables the attachment component to be capable of stretching out and lengthening along its longitudinal axis when subjected to a tensile load. In this respect, the attachment component may be stretched or otherwise elongated to either couple or decouple the prosthesis 200 with the attachment component. In particular, when the attachment component is in a stretched or otherwise elongated position (i.e. when one or both ends of the attachment component are pulled), the prosthesis 200 may more easily slide onto or off from the ends of the attachment component. As mentioned above, the curved ends of the attachment component may be configured to assist in retaining the prosthesis on the attachment component. By applying tension to the attachment component, the curved ends may straighten out which may make it easier to either couple or decouple the prosthesis to the attachment component. Once the prosthesis is in its desired position on the attachment component, the tension may be removed which may cause the curved ends of the attachment component to spring back into a more curved or coiled state to prevent the prosthesis from undesirably decoupling from the attachment component. When the attachment component is in its normal non-stretched position (such as in the configurations illustrated in FIGS. 2-7) the C-shaped, S-shaped, and/or otherwise loop or curved shaped ends of the attachment components may assist in coupling and/or retaining the prosthesis 200 with the attachment component.

Although FIGS. 2-7 illustrate various embodiments of attachment components according to aspects of the present invention, it should also be recognized that the invention is not limited to these specific configurations.

Turning now to FIGS. 8-26, various embodiments of the expandable device will now be discussed in greater detail. It should also be recognized that the expandable device 100 may be formed from a variety of materials, as the invention is not limited in this respect. In one embodiment, the expandable device is formed of polyurethane, and may, for example, be formed of nylon coated polyurethane. In one embodiment, a coating such as a thermoplastic polyurethane (TPU) coating is employed. In an embodiment where the expandable device 100 is inflatable, the expandable device may be formed of two layers of nylon coated polyurethane that together form a chamber for the introduction of air.

Applicant recognized that the expandable device may be shaped and configured in a variety of different ways. Applicant also recognized that it may be desirable for the expandable device to be configured such that the maximum dimension of the hernia repair device is minimized in its reduced configuration. As discussed below, certain aspects of the present invention are directed to an expandable device configured such that the width of the expandable device is minimized in the region where the width of the prosthesis is the greatest. As mentioned above, the portions of the prosthesis and/or expandable device which have the maximum width may correspond to the portions of the hernia repair device which have the maximum dimension when the device is manipulated into its reduced configuration. Thus, offsetting the maximum width portions of the expandable device from the maximum width portions of the prosthesis may help to minimize the maximum dimension of the device in its reduced configuration. For example, as mentioned above, and as illustrated in FIG. 1A, in one embodiment, the prosthesis is substantially elliptical shaped. In this embodiment, the width of the prosthesis is greatest in the center, along axis 120. Thus, in embodiment of the present invention, the width of the center portion of the expandable device is less than the width of an end portion of the expandable device. In this respect, the widest portion of the expandable device is not located near the widest portion of the prosthesis. When the hernia repair device is manipulated into a reduced configuration about the first axis 110, the widest portions of the expandable device 100 are then offset from the widest portions of the prosthesis 200. This helps to minimize the maximum dimension of the hernia repair device in its reduced configuration.

Although many of the below-described expandable devices are configured for use with a substantially elliptical-shaped prosthesis, the invention is not limited in this respect. The invention also is directed to expandable devices which are designed for use with a prosthesis having a different shape, where the widest portion of the expandable device is offset from the widest portion of the prosthesis.

As shown in FIG. 8, in one embodiment the expandable device 400 includes an expandable first or forward portion 402 spaced apart from an expandable second or rear portion 406 with a single intermediate portion 404 positioned there between connecting the forward portion 402 to the rear portion 406. In one embodiment, the single intermediate portion 404 is expandable. However, it is also contemplated that the single intermediate portion 404 may be non-expandable. As discussed above, the expandable device 400 has a first axis 110 and the expandable device 400 is configured to be furled, rolled or otherwise manipulated about its first axis 110 into a reduced configuration for insertion into a body. The expandable device may also have a second axis 112 which is substantially perpendicular to the first axis 110. In this illustrative embodiment, the second axis 112 may define a maximum width of the prosthesis 200, and in one particular embodiment, such as when the prosthesis is elliptical shaped, the first axis may intersect the second axis substantially at the center of the expandable device 400.

As illustrated, the expandable forward and rear portions 402, 406 of the expandable device 400 each include sections that extend outwardly from the first axis 110. These sections help to unfurl and retain the prosthesis in a planar configuration once the hernia repair device is inserted into the body. In one embodiment, the expandable forward and rear portions 402, 406 may be shaped to extend along the perimeter of the prosthesis. The single intermediate portion 404 of the expandable device is configured to align with the widest portion of the prosthesis. Applicant recognized that by strategically placing only a single intermediate connector 404 in the portion of the expandable device that corresponds to the maximum width portion of the prosthesis that the maximum dimension of the hernia repair device in its manipulated reduced configuration can be desirably decreased.

To minimize the maximum dimension of the hernia repair device in its reduced configuration, the maximum dimension of the single intermediate portion 404 in a reduced configuration is less than the maximum dimension of the expandable device 400 at either the expandable forward or rear portion 402, 406 in a reduced configuration. In particular, the maximum dimension of the intermediate portion 404 in a reduced configuration along a plane $P_c$ defined by the second axis 112 is less than the maximum dimension of either the forward or rear portion 402, 406 in a reduced configuration defined along a plane $P_f$, $P_r$ that is substantially parallel to the second axis. Such a configuration may be desirable for use with a prosthesis as discussed above, which has a widest portion aligned with the second axis 112.

In the embodiment illustrated in FIG. 8, the single intermediate portion 404 extends across approximately a center third of the expandable device 400. It should be appreciated that in another embodiment, the intermediate portion 404 may extend over more or less of the expandable device. For example, in another embodiment (shown in FIG. 10 and discussed below), the intermediate portion of the expandable device extends across approximately a center half of the expandable device.

As also illustrated in FIG. 8, in one embodiment, the single intermediate portion 404 extends substantially along the first axis 110 about which the expandable device is configured to be furled, rolled or otherwise manipulated. And as shown in FIG. 8, in one embodiment, the intermediate portion 404 is substantially linear.

FIG. 9 illustrates another embodiment of an expandable device 410 which includes an expandable forward portion 412 spaced apart from an expandable rear portion 416 with a single intermediate portion 414 positioned there between connecting the forward portion 412 to the rear portion 416. In this embodiment, the single intermediate portion 414 is expandable. As shown, both the forward and rear portions 412, 416 have hook-shaped ends that extend outwardly away from the first axis 110 and then curve inwardly back toward the first axis 110. These hook-shaped ends may be shaped to extend along the perimeter of the prosthesis. Although both the forward and rear portions 412, 416 are each illustrated with two hook-shaped ends, it should be appreciated that in another embodiment only one of the forward and rear portions 412, 416 may include a hook-shaped end, as the invention is not so limited. Furthermore, although the forward and rear portions 412, 416 have a similar shape and configuration, it is also recognized that the forward portion 412 may be shaped and configured differently from the rear portion 416.

FIG. 10 illustrates yet another embodiment of an expandable device 420 which includes an expandable forward portion 422 spaced apart from an expandable rear portion 426 with a single intermediate portion 424 positioned there between connecting the forward portion 422 to the rear portion 426. As shown, both the forward and rear portions 422, 426 have substantially C-shaped ends that extend outwardly away from the first axis 110 that may be shaped to extend along the perimeter of the prosthesis. Although both the forward and rear portions 422, 426 are each illustrated with two substantially C-shaped ends, it should be appreciated that in another embodiment only one of the forward and rear portions 422, 426 may include a C-shaped end, as the invention is not so limited. In this particular embodiment, the single intermediate portion 424 extends in a substantially linear direction along the first axis 110 and extends across approximately a center half of the expandable device 420. In this embodiment, the forward portion 422 extends across approximately only one quarter of the expandable device, and similarly, the rear portion 426 also only extends across approximately one quarter of the expandable device 420.

FIG. 11 similarly illustrates yet another embodiment of an expandable device 430 which includes an expandable forward portion 432 spaced apart from an expandable rear portion 436 with a single intermediate portion 434 positioned there between. In this particular embodiment, both the forward and rear portions 432, 436 include a substantially linear portion and the intermediate portion 434 is also substantially linear. As shown, the substantially linear portions of the forward and rear portions 432, 436 are angled with respect to the linear intermediate portion 434. Although both the forward and rear portions 432, 436 are each illustrated with substantially linear ends, it should be appreciated that in another embodiment only one of the forward and rear portions 432, 436 may include a linear end, as the invention is not so limited.

The expandable device 440 illustrated in FIG. 12 also has expandable forward and rear portions 442, 446 which include substantially linear portions and a single substantially linear intermediate portion 444.

Furthermore, like the embodiment shown in FIG. 9, the expandable device 450 illustrated in FIG. 13 also has expandable forward and rear portions 452, 456 that are connected via a single intermediate portion 454. The forward and rear portions 452, 456 each have hook-shaped ends that extend outwardly away from the first axis 110 and then curve inwardly back toward the first axis 110.

Figure 14:
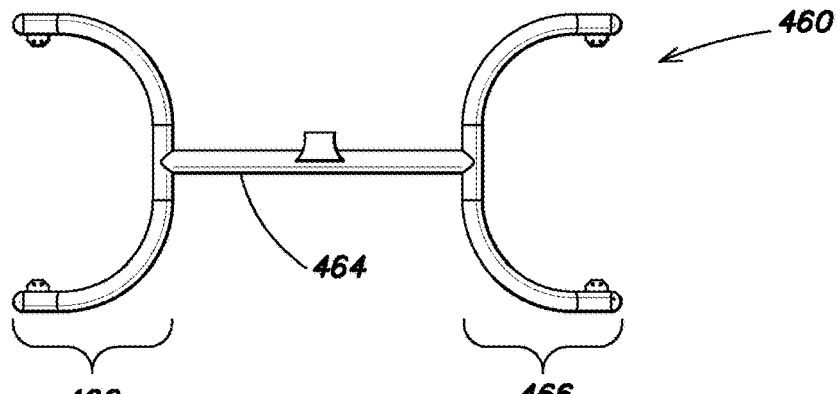

FIG. 14 illustrates yet another embodiment of an expandable device 460 which is similar to the embodiment illustrated in FIG. 10 in that it includes an expandable forward portion 462 spaced apart from an expandable rear portion 466 with a single intermediate portion 464 positioned there between with both the forward and rear portions 462, 466 having substantially C-shaped ends that extend outwardly away from the first axis 110.

Figure 15:
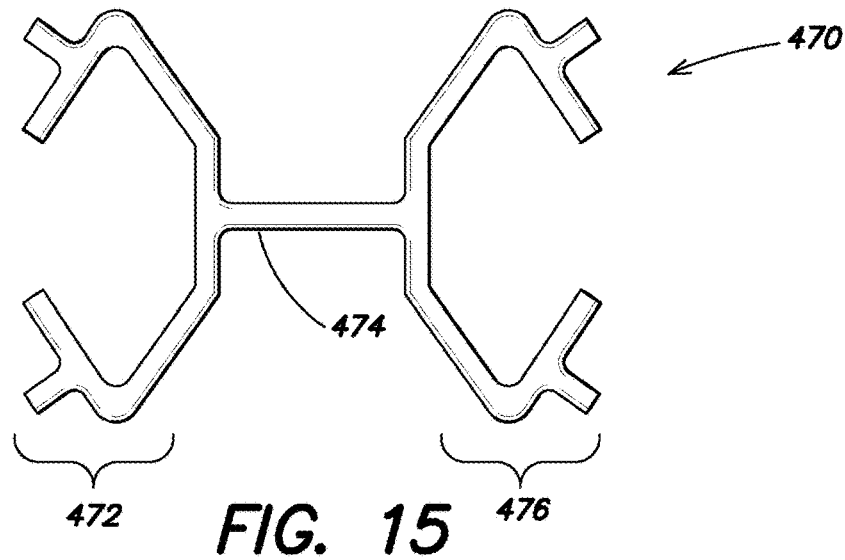

The embodiment illustrated in FIG. 15 includes an expandable device 470 which includes a more angular shaped expandable forward portion 472 and expandable rear portion 476, each made up of a plurality of substantially linear segments, with a single intermediate portion 474.

Figure 16:
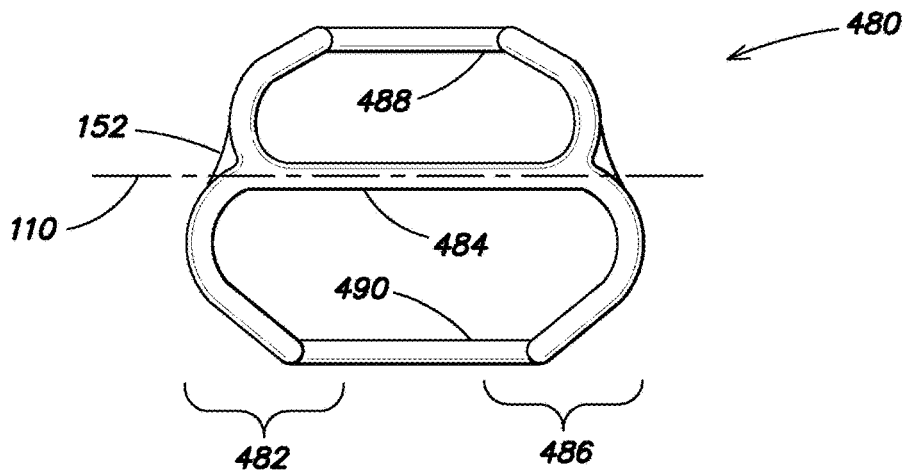

FIG. 16 illustrates another embodiment of an expandable device 480 which also includes an expandable forward portion 482, an expandable rear portion 486 and a single intermediate portion 484 positioned there between connecting the forward portion 482 to the rear portion 486. In one particular embodiment, the expandable forward portion 482, expandable rear portion 486 and single intermediate portion 484 are inflatable. The overall shape of the inflatable portion of this expandable device 480 is similar to the overall shape of the expandable device 420 illustrated in FIG. 10. In addition, the expandable device 480 may also includes non-expandable portions 488, 490 which extend between and connect the forward and rear portions 482, 486. As mentioned above, in an embodiment where the expandable device 100 is inflatable, the expandable device may be formed of two layers of nylon coated polyurethane that together form a chamber for the introduction of air. In such a configuration, the non-expandable portions 488, 490 may be formed of only one layer of material, such as one layer of nylon coated polyurethane. These non-expandable portions 488, 490 are non-inflatable, but may still assist in retaining the overall shape of the expandable device 480. Furthermore, in this embodiment, because the non-expandable portions 488, 490 are formed of only one layer of the nylon material, in comparison to the two layers of the same nylon material used to form the other portions of the expandable device 480, the maximum dimension of the center portion of the expandable device in a reduced configuration (which includes the single intermediate portion 484 and the non-expandable portions 488, 490) may be less than the maximum dimension of the expandable device 480 in a reduced configuration at either the forward or rear portion 482, 486.

FIG. 17 illustrates another embodiment of an expandable device 500 which in some respects is similar to the expandable device 420 disclosed in FIG. 10, including an expandable forward portion 502, an expandable rear portion 506 and a single intermediate portion 504 positioned there between connecting the forward portion 502 to the rear portion 506. However, in the embodiment illustrated in FIG. 17, the single expandable intermediate portion 504 is offset from the first axis 110.

The embodiment of the expandable device 510 illustrated in FIG. 18 is similar in some respects to the expandable device 500 shown in FIG. 17 in that it includes an expandable forward portion 512, an expandable rear portion 516 and a single intermediate portion 514 positioned there between connecting the forward portion 512 to the rear portion 516, with the intermediate portion 514 is offset from the first axis 110. However, in the embodiment illustrated in FIG. 18, the intermediate portion 514 is nonlinear and is substantially W-shaped.

The embodiment of the expandable device 520 illustrated in FIG. 19 is also similar to FIG. 18, having an expandable forward portion 522, an expandable rear portion 526 and a single intermediate portion 524 positioned there between connecting the forward portion 522 to the rear portion 526, with the intermediate portion 524 offset from the first axis 110. However, in the embodiment illustrated in FIG. 19, the intermediate portion 524 is substantially linear. In this particular embodiment, the forward portion 522, the rear portion 526 and the intermediate portion 524 together are substantially U-shaped.

Figure 20:
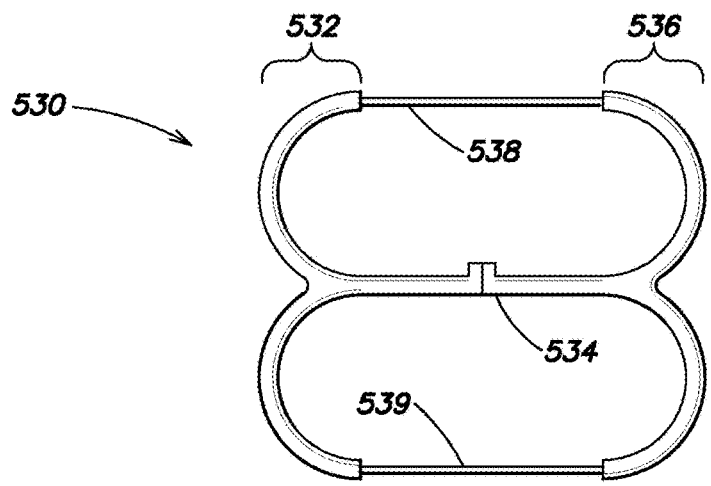

FIG. 20 illustrates yet another embodiment of an expandable device 530 that in some respects is similar to the expandable device 480 shown in FIG. 16 in that it includes an inflatable portion which includes an expandable forward portion 532, an expandable rear portion 536 and a single intermediate portion 534 which extends along the first axis 110. In addition, the expandable device 530 also includes non-expandable portions 538, 539 which extend between and connect the forward and rear portions 532, 536. These non-expandable portions 538, 540 are non-inflatable, but may assist in retaining the overall shape of the expandable device 530. Furthermore, in this particular embodiment, these non-expandable portions 538, 539 are formed of a thin layer of a material, such as a suture material, so that the maximum dimension of the center portion of the expandable device in a reduced configuration (which includes the single expandable intermediate portion 534 as well as the non-expandable portions 538, 539) is less than the maximum dimension of either the forward or rear portion 532, 536 in the reduced configuration.

Figure 21:
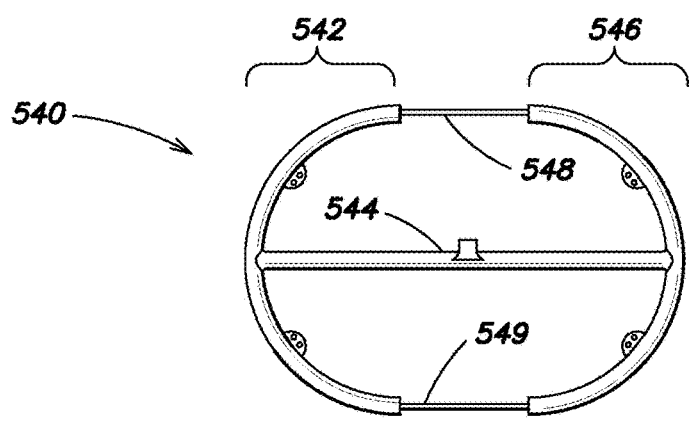

The embodiment of the expandable device 540 illustrated in FIG. 21 is similar to the expandable device 530 illustrated in FIG. 20 except that the shape of the expandable forward and rear portions 542, 546 is configured differently. The expandable device 540 also includes a single intermediate portion 544 which extends substantially along the first axis 110 of the device 540. The device 540 also includes non-expandable portions 548, 549, which may be made of suture material, extending between and connect the forward and rear portions 542, 546. The non-expandable portions 548, 549 may be configured to retain the shape of the expandable device when in an expanded or planar configuration.

Figure 22:
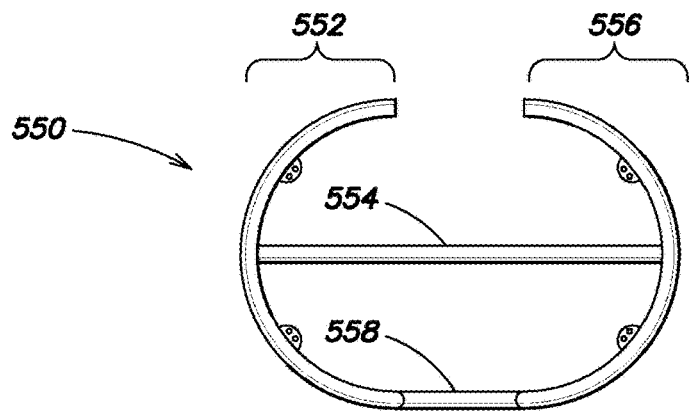

FIG. 22 illustrates another embodiment of an expandable device 550 which includes an expandable forward portion 552, an expandable rear portion 556 and a single intermediate portion 554. The intermediate portion 554 includes a substantially linear inflatable segment connecting the forward and rear portions 552, 556 along the first axis 110 of the expandable device 550. The device 550 also includes a substantially linear non-inflatable portion 558 which is offset from the first axis 110. As discussed above, the non-inflatable portion 558 may be formed of a thin layer of material, so that the maximum dimension of the center portion of the device 550 in the reduced configuration is less than the maximum dimension of either the forward or rear portion 552, 556 in the reduced configuration. These non-inflatable portions 558 may be configured to hold the shape of the expandable device when in a planar configuration.

Figure 23:
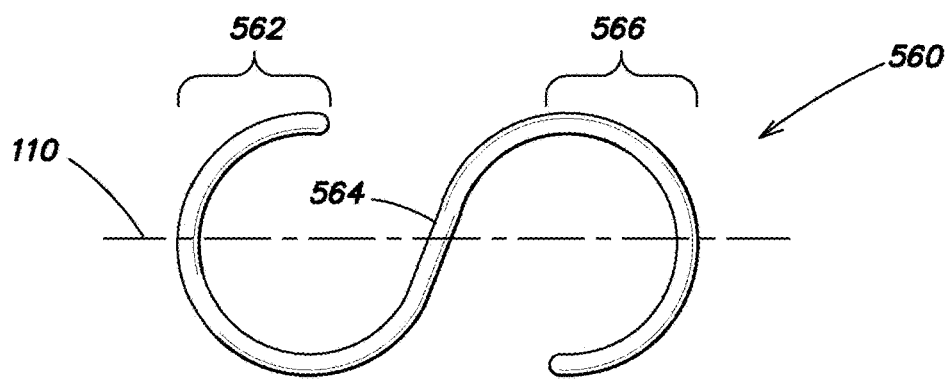
Figure 24:
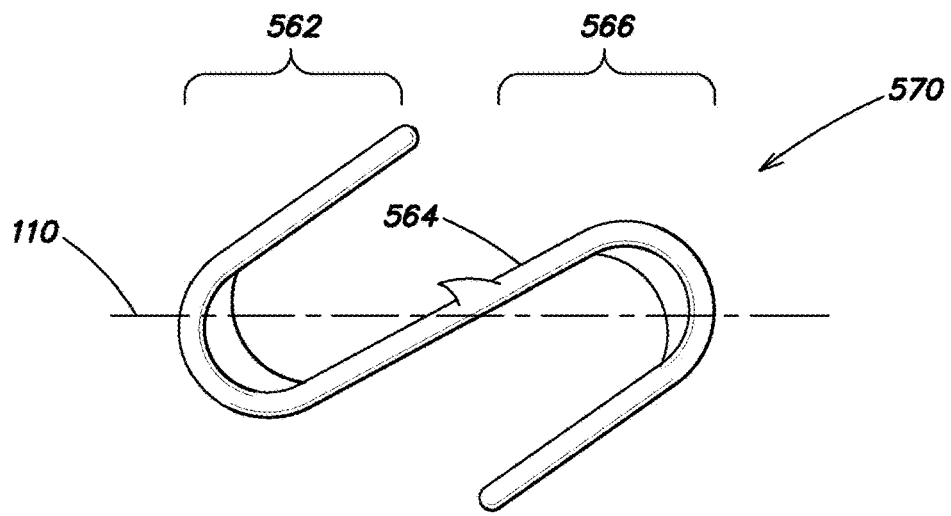

FIGS. 23 and 24 illustrate additional embodiments of the expandable device 560, 570, both of which have a substantially S-shaped configuration. Each device 560, 570 includes an expandable forward portion 562, an expandable rear portion 566 and a single intermediate portion 564 extending between and connecting the forward portion 562 and the rear portion 566. In both of these embodiments, the intermediate portion 564 extends substantially along a diagonal relative to the first axis 110.

Figure 25:
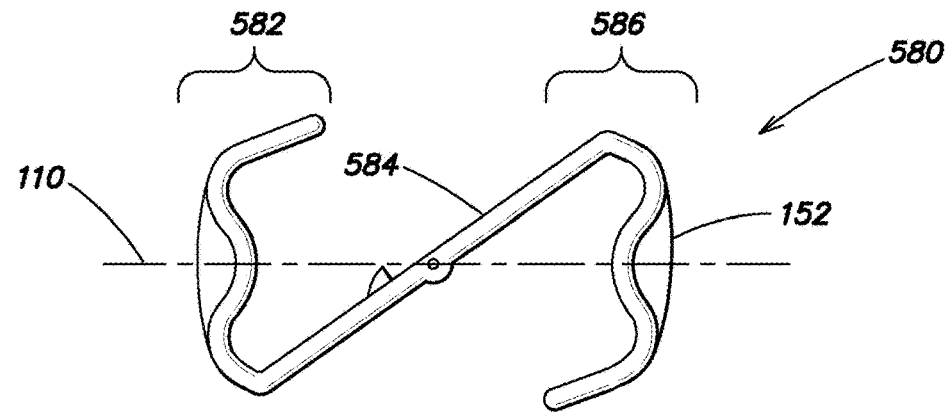

FIG. 25 also illustrates an additional embodiment of the expandable device 580 which has a single intermediate portion 584 that extends substantially along a diagonal relative to the first axis 110. The expandable device 580 shown in FIG. 25 has an expandable forward portion 582 and an expandable rear portion 586 which form approximately an N-shaped expandable device 580 with the intermediate portion 584, and the maximum dimension of the intermediate portion 584 in the reduced configuration is less than the maximum dimension of either the forward or rear portion 582, 586 in the reduced configuration.

Figure 26:
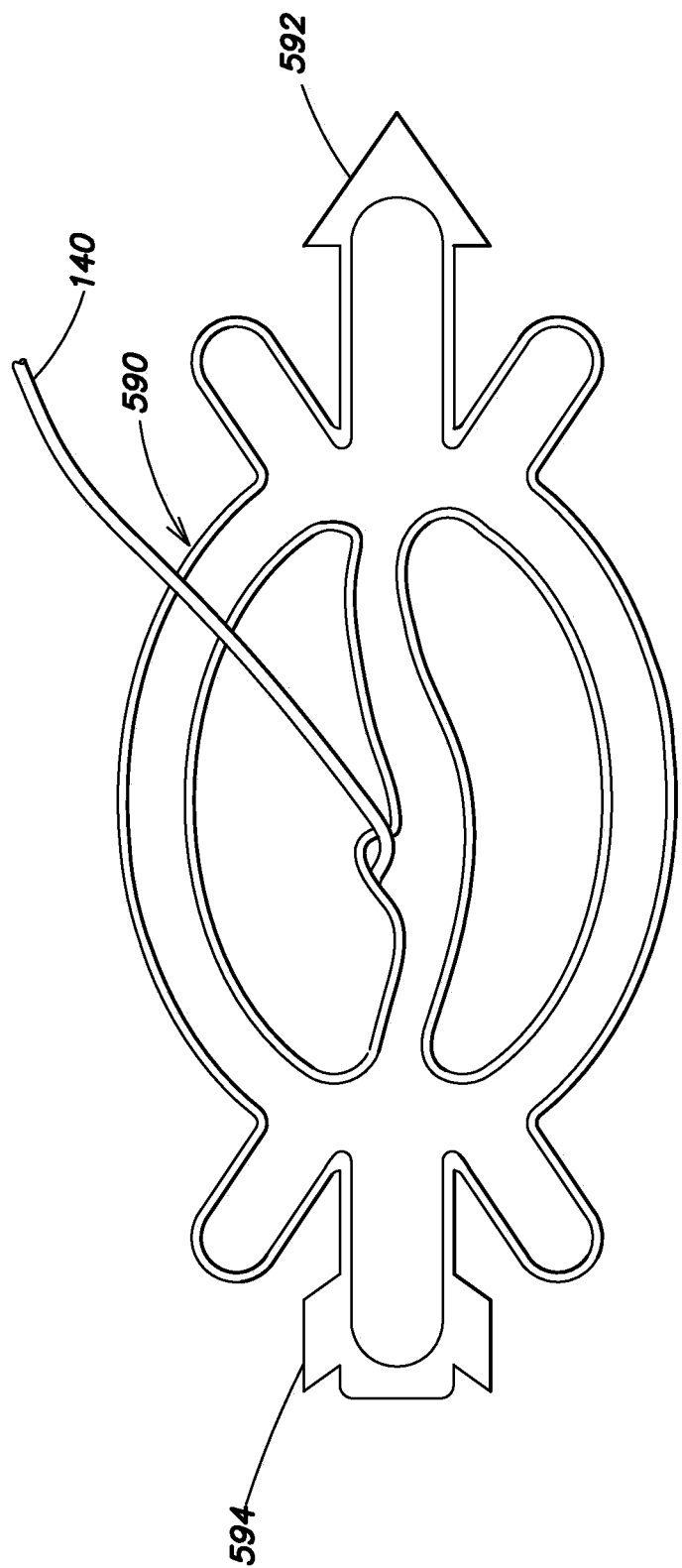

FIG. 26 illustrates a further embodiment of an expandable device 590 according to the present invention. In some respects, this expandable device is configured similar to the expandable device 100 shown in FIG. 1A. In contrast, the expandable device 590 includes indicia 592, 594 on each end of the expandable device 590 which indicate the superior and inferior ends of the device. Such indicia 592, 594 may assist the user in positioning the expandable device 590 and the prosthesis 200 within the body. In this particular embodiment, the indicia 592, 594 are configured as arrow head and an arrow end, but it should be appreciated that other types of indicia, such as numbers, letters, arrows, or other various markings, may be used as the invention is not so limited.

With the soft tissue repair prosthesis deployed and expanded in the intra-abdominal space, a suture-grasping device (not shown) may be provided to grasp and hoist the prosthesis 200 towards the defect and/or to position the soft tissue repair prosthesis against the abdominal wall. Once the soft tissue repair prosthesis 200 is positioned relative to the defect, sutures, fasteners, adhesives or the like may be applied to fixate the prosthesis 200 in place.

After placement of the prosthesis 200, the attachment components may be left in place or, instead, removed. As an example, and without limitation, an instrument may be employed to remove the attachment components. In one embodiment, the attachment components are resorbable.

A method of repairing a hernia defect in accordance with the present invention includes one or more of the acts of: detachably securing an expandable device to a prosthesis, rolling, folding or otherwise manipulating the prosthesis and detachably secured expandable device into a slender configuration, inserting the prosthesis and expandable device into the intra-intra-abdominal space, inflating or otherwise expanding the expandable device to unfurl the mesh, hoisting the prosthesis up against the abdominal wall, fixating the prosthesis against the abdominal wall, detaching the expandable device from the prosthesis, and removing the attachment components and the expandable device from the intra-intra-abdominal space.

A method of assembling a hernia repair device in accordance with the present invention includes one or more of the acts of: arranging a soft tissue repair prosthesis on an expandable device with at least one attachment component, where the prosthesis, expandable device and attachment component form a hernia repair device, and manipulating the hernia repair device about a first axis into a reduced configuration, where the soft tissue repair prosthesis is arranged on the expansion device such that a maximum dimension of the hernia repair device in the reduced configuration is minimized.

Turning back to FIG. 1A, in one embodiment, the attachment components 300a-d are positioned to extend entirely within the perimeter (i.e. the outer boundary) of the expandable device 100. In other words, portions of the attachment components 300a-d do not extend beyond the perimeter of the expandable device 100. Applicant recognized that when suturing the prosthesis to the abdominal wall, the user may inadvertently pass the suture through the attachment component. Applicant further recognized that it may be desirable to position the attachment components to extend entirely within the perimeter of the expandable device to minimize the risk of inadvertently fixing the attachment components to the prosthesis when the prosthesis is, for example, being fastened to the abdominal wall.

Once the prosthesis 100 is positioned against the abdominal wall, it may be difficult for a user to visually detect the location of all of the attachment components. For example, the prosthesis may be opaque and thus the user may not see portions of the attachment component that extend behind the prosthesis. Applicant recognized that the user will be able to visually detect the location of the expandable device. Thus, the user may be able to more easily avoid inadvertently fixing the prosthesis to the expandable device when the prosthesis is being fastened to the abdominal wall. By placing the attachment components entirely within the perimeter of the expandable device 100, then when the user avoids the expandable device when securing the prosthesis to the wall, the user will also then avoid securing the attachment components to the prosthesis.

As shown in FIG. 1A, in one embodiment, the expandable device 100 may include both an expandable portion 150 and a non-expandable portion 152. In this particular embodiment, the non-expandable portion 152 is formed around the perimeter of the expandable portion 150 and substantially follows the shape of the expandable portion 150.

Applicant recognized that in some embodiments, it may be desirable to arrange the attachment components to extend within the non-expandable portion 152. For example, it may be desirable to arrange the attachment components within the non-expandable portion 152 in an embodiment where the expandable device is inflatable. By placing the attachment components, which may include a sharp end, away from the inflatable expandable portion 150, a user may be less likely to puncture or otherwise damage the expandable device. As shown in FIG. 1A, the expandable device may include a non-expandable portion 152 with substantially circular shaped portions at locations spaced around the outer portion of the expandable device configured for the placement of the attachment components 300a-d.

As shown in FIGS. 8, 10, 12, 16, 18, 19 and 25, the expandable device may include a non-expandable portion 152 positioned on the ends of the expandable device, and as illustrated, such non-expandable portions 152 may be arranged on the first axis 110 (furling axis) to provide a tab for the user to grasp the expandable device 100 while minimizing the risk of damaging the expandable portions.

Figure 27:
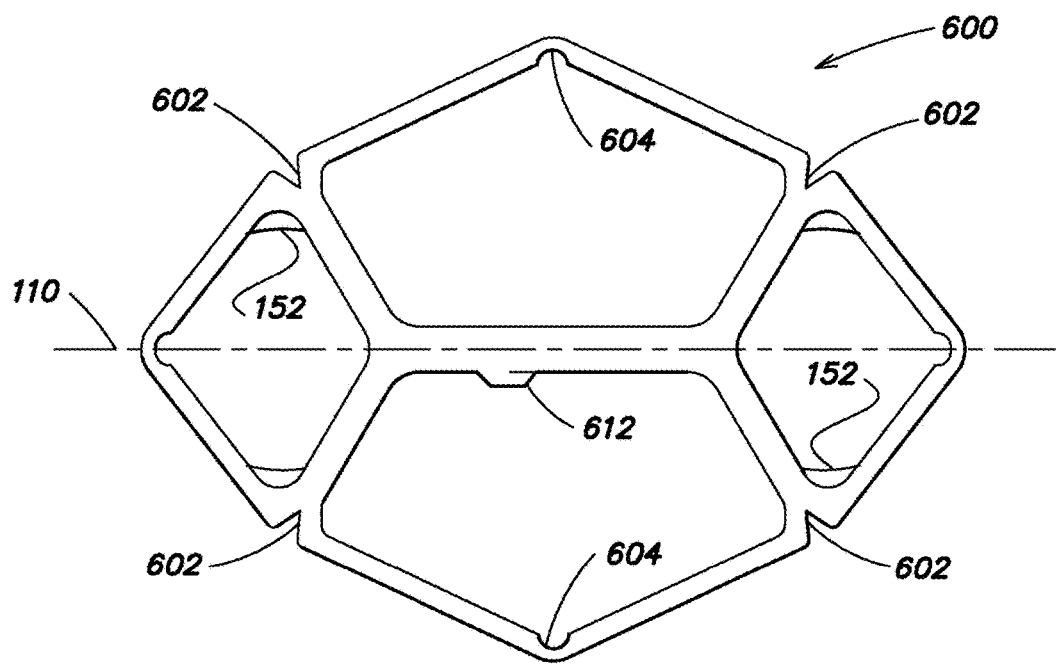
Figure 28:
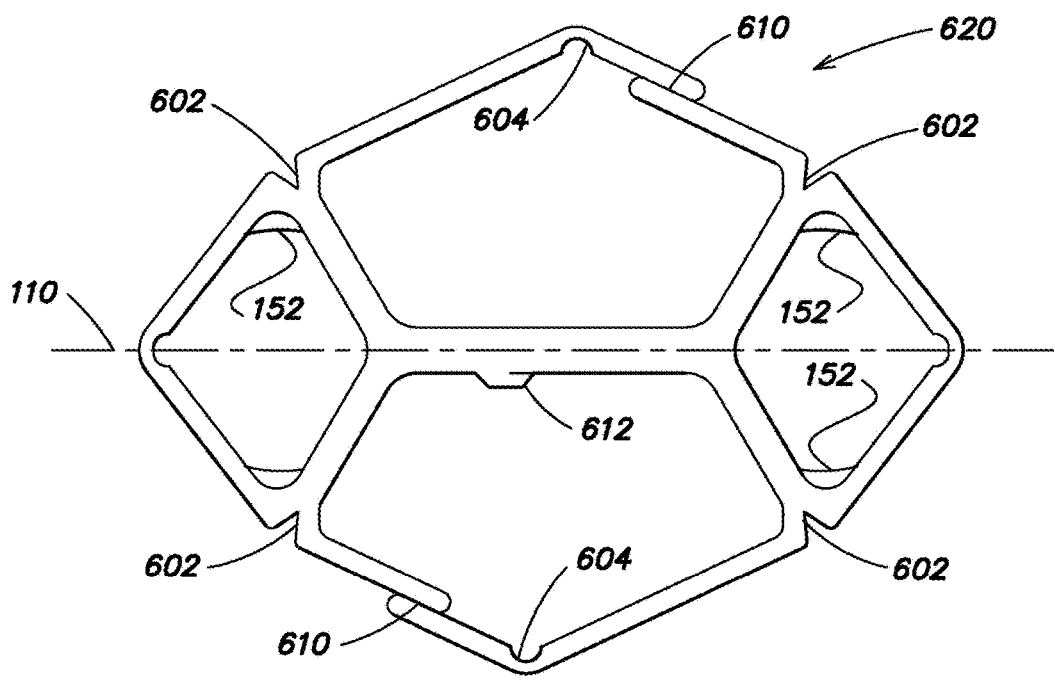

FIGS. 27 and 28 illustrate further embodiments of an expandable device 600, 620 according to aspects of the present invention. In one embodiment, these expandable devices 600, 620 are inflatable, and as discussed above, these devices 600, 620 are configured to be removably connected with a soft tissue repair prosthesis and when deflated, are configured to be manipulated about a first axis 110 into a reduced configuration for insertion into a body.

Applicant recognized that when the expandable device is inflated and transformed from a substantially two-dimensional configuration to a three-dimensional configuration that the device may bend, bow or twist such that the three-dimensional inflated configuration may not be a substantially planar configuration. Applicant determined that this bending may be more prominent at the perimeter of the expandable device.

In some circumstances, it may be desirable for the three-dimensional inflated configuration to have a substantially planar configuration. In other circumstances, it may be desirable for the three-dimensional inflated configuration to have a substantially curved configuration, but it may be desirable for the device to only curve or bend to a certain degree. For example, when the inflatable device is used to position a prosthesis adjacent a hernia defect in an abdominal wall, it may be desirable for the curvature of the device to follow the contour of the abdominal wall.

Thus, Applicant developed an approach to minimize the bending of the inflatable device when inflated. In particular, as illustrated in FIGS. 27 and 28, in one embodiment, the inflatable devices include a plurality of reliefs 602, 604 spaced around the perimeter of the inflatable device 600, 620 which are configured to minimize bending of the inflatable device when inflated. Applicant recognized that the undesirable bending of the inflatable device may occur in regions of the device where the cross-section or diameter of the device is not constant (such as at a joint where multiple inflatable portions intersect). Thus, as shown, the reliefs 602, 604 may be positioned in these areas where the cross section of the device is not constant. The reliefs 602, 604 may act to minimize the variation in the cross-section or diameter of the device such that the device is inflated more evenly and with less twisting.

In one illustrative embodiment, a relief 602, 604 is configured as a notch, whereas in another embodiment, a relief 602 may be configured as a slit. In the illustrative embodiment, a plurality of substantially V-shaped notches 602 are positioned around the perimeter of the device and are outwardly facing to allow the device to open outwardly as it is inflated. As shown, the device 600, 620 may also include reliefs 604 that are substantially U-shaped that are positioned around the perimeter of the device and are inwardly facing to allow the device to open inwardly as it is inflated. In some respects, these reliefs 602, 604 help to control where and/or to what degree the device 600, 620 bends as it is inflated.

In one embodiment, the reliefs 602, 604 are configured such that the inflatable device 600, 620 is substantially planar when inflated into its three dimensional configuration. In another embodiment, the reliefs 602, 604 are configured such that the inflatable device has a substantially curved configuration when inflated into its three-dimensional configuration. The reliefs 602, 604 may be configured to minimize the amount of bending which occurs such that a predetermined desired curved configuration is achieved, for example, to follow the contour of the abdominal wall.

The embodiment illustrated in FIG. 28 is similar to the one disclosed in FIG. 27, except that the inflatable device 620 in FIG. 28 includes a plurality of seams 610 which separate portions of the inflatable device. These seams 610 may assist to make inflation of the device 620 more uniform. In one embodiment, the seams 610 may be welded. The inflatable device 600, 620 may be inflated with an inflation tube (not shown) that may connect to the device 600, 620 at an inflation port 612 positioned approximately at the center of the device. Furthermore, the device 600, 620 may include a plurality of non-expandable portions 152, and as mentioned above, it may be desirable to arrange the attachment components within the non-expandable portions 152 in an embodiment where the expandable device is inflatable.

The prosthesis 200 may be formed of a porous material, such as a knit, woven or non-woven fabric, or may be composed of a solid, substantially non-porous, or microporous material. The prosthesis may be formed of one or more layers of the same or dissimilar material. The prosthesis may be formed with portions that are tissue infiltratable and other portions that are non-tissue infiltratable, providing selected areas of the repair device with different tissue ingrowth and adhesion resistant properties. The prosthesis may be formed of permanent material, resorbable material, or a combination of permanent and resorbable materials. It should be appreciated that the prosthesis may be formed of any biologically compatible material, synthetic or natural, suitable for repairing a tissue or muscle wall defect as would be apparent to one of skill in the art. The prosthesis may be formed into a patch, plug or combination patch and plug.

In one embodiment, the prosthesis 200 is formed from a mesh fabric, such as a sheet of knitted polypropylene monofilament mesh fabric. The sheet may have a thickness of approximately 0.014 inches and may be knitted from polypropylene monofilament having a diameter of approximately 0.0042 inches. When implanted, the polypropylene mesh promotes rapid tissue or muscle ingrowth into and around the mesh structure. Alternatively, other surgical materials which are suitable for tissue or muscle reinforcement and defect correction may be utilized including BARD MESH (available from C.R. Bard, Inc.), SOFT TISSUE PATCH (microporous ePTFE—available from W.L. Gore & Associates, Inc.); SURGIPRO (available from US Surgical, Inc.); TRELEX (available from Meadox Medical); PROLENE and MERSILENE (available from Ethicon, Inc.); and other mesh materials (e.g., available from Atrium Medical Corporation). Biologic materials, including XENMATRIX, COLLAMEND, and ALLOMAX (all available from C.R. Bard, Inc.) or COOK SURGISIS (available from Cook Biomedical, Inc.) may also be used. Resorbable materials, including polyglactin (VICRYL—available from Ethicon, Inc.) and polyglycolic acid (DEXON—available from US Surgical, Inc.), may be suitable for applications involving temporary correction of tissue or muscle defects. The fabric may be formed from multifilament yarns and that any suitable method, such as knitting, weaving, braiding, molding and the like, may be employed to form the mesh material. It should be appreciated that when the soft tissue repair prosthesis is in the form of a sheet, it may be configured in many shapes, including, but not limited to flat, concave, and convex, and may, for example, be in the form of a square, rectangle, circle, or ellipse.

The present invention also contemplates other systems for expanding and/or unfurling the prosthesis. Although inflatable expandable devices (either filled with a gas or a liquid) are primarily discussed above, other expandable devices that do not rely on inflation are contemplated. For example, and without limitation, also contemplated are an expandable device that includes telescoping portions and/or umbrella-like spokes, an expandable device including shape memory material, and an expandable device that resiliently expands into an enlarged configuration.

It should be appreciated that various embodiments of the present invention may be formed with one or more of the above-described features. The above aspects and features of the invention may be employed in any suitable combination as the present invention is not limited in this respect. It should also be appreciated that the drawings illustrate various components and features which may be incorporated into various embodiments of the present invention. For simplification, some of the drawings may illustrate more than one optional feature or component. However, the present invention is not limited to the specific embodiments disclosed in the drawings. It should be recognized that the present invention encompasses embodiments which may include only a portion of the components illustrated in any one drawing figure, and/or may also encompass embodiments combining components illustrated in multiple different drawing figures.

It should be understood that the foregoing description of various embodiments of the invention are intended merely to be illustrative thereof and that other embodiments, modifications, and equivalents of the invention are within the scope of the invention recited in the claims appended hereto.

The invention claimed is:

1. A hernia repair device, comprising: an inflatable device configured to be removably connected with a soft tissue repair prosthesis, the inflatable device having a first inflatable segment and a second inflatable segment, the first inflatable segment having a first closed end such that there is no fluid communication through the first closed end, and the second inflatable segment extending past the first closed end and overlapping with a portion of the first inflatable segment over a region of overlap;
   wherein fluid communication between the first and second inflatable segments is closed along the entire region of overlap.

2. The hernia repair device of claim 1, wherein the second inflatable segment has a second closed end that is spaced from the first closed end.

3. The hernia repair device of claim 1, wherein the inflatable device includes a seam between the first and second inflatable segments that closes fluid communication between the first and second inflatable segments along the region of overlap.

4. The hernia repair device of claim 3, wherein the seam is welded.

5. The hernia repair device of claim 1, wherein, at the region of overlap, the first inflatable segment is at an outermost perimeter of the inflatable device.

6. The hernia repair device of claim 5, wherein a portion of the second inflatable segment excluding the region of overlap is at the outermost perimeter of the inflatable device.

7. The hernia repair device of claim 1, wherein the first inflatable segment has a first longitudinal axis running lengthwise through the first inflatable segment and the second inflatable segment has a second longitudinal axis running lengthwise through the second inflatable segment, the first longitudinal axis maintaining a constant distance from the second longitudinal axis along the region of overlap.

8. The hernia repair device of claim 1, wherein the first inflatable segment has a length that is longer than the region of overlap.

9. The hernia repair device of claim 1, wherein the first and second inflatable segments are in fluid communication with one another.

10. The hernia repair device of claim 1, wherein the inflatable device has a first axis wherein, when deflated, the inflatable device is configured to be manipulated about the first axis into a reduced configuration for insertion into a body.

11. The hernia repair device of claim 10, wherein the inflatable device has an intermediate segment extending along the first axis and a first outer segment that bows away from the intermediate segment, the first outer segment being formed by the first and second inflatable segments.

12. The hernia repair device of claim 11, wherein a first through-hole opening is defined between the intermediate segment and the first outer segment.

13. The hernia repair device of claim 11, wherein the inflatable device has a second outer segment that bows away from the intermediate segment on an opposite side of the intermediate segment relative to the first outer segment, the second outer segment being formed by a third inflatable segment and a fourth inflatable segment, the third inflatable segment having a third closed end and the fourth inflatable segment extending past the third closed end and overlapping with a portion of the third inflatable segment over a second region of overlap.

14. The hernia repair device of claim 13, wherein a second through-hole opening is defined between the intermediate segment and the second outer segment.

15. A hernia repair device, comprising:
an inflatable device configured to be removably connected with a soft tissue repair prosthesis, the inflatable device having a first inflatable segment and a second inflatable segment that overlaps with the first inflatable segment along a region of overlap defined by a seam, the first inflatable segment being positioned on an outer side relative to the second inflatable segment closer to an outermost perimeter of the inflatable device at the region of overlap.

16. The hernia repair device of claim 15, wherein the seam closes fluid communication between the first and second inflatable segments along the region of overlap.

17. The hernia repair device of claim 16, wherein the seam is welded.

18. A hernia repair device, comprising: an inflatable device configured to be removably connected with a soft tissue repair prosthesis, the inflatable device having a first inflatable segment and a second inflatable segment, the first inflatable segment having a first closed end such that there is no fluid communication through the first closed end, and the second inflatable segment extending past the first closed end and overlapping with a portion of the first inflatable segment over a region of overlap;
wherein, at the region of overlap, the first inflatable segment is at an outermost perimeter of the inflatable device.

19. The hernia repair device of claim 18, wherein a portion of the second inflatable segment excluding the region of overlap is at the outermost perimeter of the inflatable device.

20. The hernia repair device of claim 18, wherein the first and second inflatable segments are in fluid communication with one another.

* * * * *

UNITED STATES PATENT AND TRADEMARK OFFICE
CERTIFICATE OF CORRECTION

PATENT NO.        : 10,166,093 B2
APPLICATION NO.   : 15/711886
DATED             : January 1, 2019
INVENTOR(S)       : Augustus Felix et al.

It is certified that error appears in the above-identified patent and that said Letters Patent is hereby corrected as shown below:

In the Specification

At Column 3, Line 44, replace "effect" with --affect--
At Column 5, Line 6, replace "delivery" with --deliver--
At Column 7, Line 57, replace "delivery" with --deliver--
At Column 12, Line 67, replace "includes" with --include--

Signed and Sealed this
Twenty-sixth Day of March, 2019

Andrei Iancu
*Director of the United States Patent and Trademark Office*